United States Patent
Becker et al.

(10) Patent No.: US 10,465,044 B2
(45) Date of Patent: Nov. 5, 2019

(54) WELL-DEFINED DEGRADABLE POLY(PROPYLENE FUMARATE) POLYMERS AND SCALABLE METHODS FOR THE SYNTHESIS THEREOF

(71) Applicants: Matthew Becker, Stow, OH (US); Howard Dean, Columbus, OH (US); Yuanyuan Luo, Akron, OH (US)

(72) Inventors: Matthew Becker, Stow, OH (US); Howard Dean, Columbus, OH (US); Yuanyuan Luo, Akron, OH (US)

(73) Assignees: THE UNIVERSITY OF AKRON, Akron, OH (US); THE OHIO STATE UNIVERSITY, Columbus, OH (US)

( * ) Notice: Subject to any disclaimer, the term of this patent is extended or adjusted under 35 U.S.C. 154(b) by 8 days.

(21) Appl. No.: 15/527,484

(22) PCT Filed: Nov. 18, 2015

(86) PCT No.: PCT/US2015/061314
§ 371 (c)(1),
(2) Date: May 17, 2017

(87) PCT Pub. No.: WO2016/081587
PCT Pub. Date: May 26, 2016

(65) Prior Publication Data
US 2017/0355815 A1 Dec. 14, 2017

Related U.S. Application Data

(60) Provisional application No. 62/139,196, filed on Mar. 27, 2015, provisional application No. 62/081,219, filed on Nov. 18, 2014.

(51) Int. Cl.
| | |
|---|---|
| *C08G 63/78* | (2006.01) |
| *C08G 63/52* | (2006.01) |
| *C08G 63/90* | (2006.01) |
| *A61L 27/56* | (2006.01) |
| *B33Y 70/00* | (2015.01) |
| *C08L 67/06* | (2006.01) |
| *A61L 27/18* | (2006.01) |

(52) U.S. Cl.
CPC .............. *C08G 63/78* (2013.01); *A61L 27/18* (2013.01); *A61L 27/56* (2013.01); *B33Y 70/00* (2014.12); *C08G 63/52* (2013.01); *C08G 63/90* (2013.01); *C08L 67/06* (2013.01)

(58) Field of Classification Search
CPC ......... C08L 67/06; B33Y 70/00; C08G 63/52; C08G 63/78; C08G 63/90; A61L 27/18; A61L 27/56
See application file for complete search history.

(56) References Cited

U.S. PATENT DOCUMENTS

| | | |
|---|---|---|
| 3,538,043 A | 11/1970 | Herold |
| 6,124,373 A | 9/2000 | Peter et al. |
| 7,649,022 B2 | 1/2010 | Gomurashvili et al. |
| 8,445,007 B2 | 5/2013 | Gomurashvili et al. |
| 8,652,504 B2 | 2/2014 | Li et al. |
| 8,765,164 B2 | 7/2014 | Katsarava et al. |
| 8,809,212 B1 | 8/2014 | Dirk et al. |
| 8,974,815 B2 | 3/2015 | Chu et al. |

FOREIGN PATENT DOCUMENTS

| | | |
|---|---|---|
| WO | 95/29710 | 11/1995 |
| WO | 02/085246 A2 | 10/2002 |

OTHER PUBLICATIONS

Kurtis Kasper et al "Synthesis of poly(propylene fumarate)", Nature Protocols, vol. 4 No. 4;518-525 (Year: 2009).*
Naoyuki Toyoda "Polymers from 1,2-Disubstituted Ethylenic Monomers VI. Monomer-Isomerization Radical Polymerization of Diethyl Maleate",Polymer Journal, vol. 15, No. 4, pp. 255-260 (1983) (Year: 1983).*
Shigenobu Takenouchi et al "Effects of Geometrical Difference of Unsaturated Aliphatic Polyesters on Their Biodegradability II. Isomerization of Poly(maleic anhydride-co-propylene oxide) in the Presence of Morpholine", Polymer Journal, vol. 34, No. 1, pp. 36-42 (2002) (Year: 2002).*
Craig B. Fryhle et al "Isomerization of Dimethyl Maleate to Dimethyl Fumarate",vol. 68 No. 12 Dec. 1991 (Year: 1991).*
Lee at al "Fabrication and Characterization of Poly(Propylene Fumarate) Scaffolds with Controlled Pore Structures Using 3-Dimensional Printing and Injection Molding", Oct. 2006 (Year: 2006).*
Sobczak "Ring-opening polymerization of cyclic esters in the presence of choline/SnOct2 catalytic system"Polym. Bull. (2012) 68: 2219-2228 (Year: 2012).*
Angela M. DiCiccio and Geoffrey W. Coates, "Ring-Opening Copolymerization of Maleic Anhydride with Epoxides: A Chain-Growth Approach to Unsaturated Polyesters," J. Am. Chem. Soc. 201, 133, 10724-10727.

(Continued)

*Primary Examiner* — Ling Siu Choi
*Assistant Examiner* — Gennadiy Mesh
(74) *Attorney, Agent, or Firm* — Renner Kenner Greive Bobak Taylor & Weber

(57) ABSTRACT

Method for making poly(propylene fumarate) (PPF) polymer made by ring-opening polymerization of propylene oxide and maleic anhydride in the presence of magnesium ethoxide initiator, wherein PPF is specifically designed for us in 3D manufacturing of medical devices. PPF polymers have a number average molecular weight (Mn) of from about 450 Daltons to about 3400 Daltons; a molecular mass distribution (Ð m) of from 1.0 to 2.0; and contains less than 1% w/w of poly(maleic anhydride-co-propylene oxide) polymer chains particularly. PPF polymers are non-toxic, degradable, and resorbable and can be used in tissue scaffolds and medical devices that are implanted within a living organism.

16 Claims, 19 Drawing Sheets

(56) References Cited

OTHER PUBLICATIONS

Shigenobu Takenouchi, Akinori Takasu, Yoshihito Inai, and Tadamichi Hirabayashi, "Effects of Geometrical Difference of Unsaturated Aliphatic Polyesters on Their Biodegradability II. Isomerization of Poly(maleic anhydride-co-propylene oxide) in the Presence of Morpholine," Polymer Journal, vol. 34, No. 1, pp. 36-42 (2002).
Shung, A.K., et al.; Kinetics of Poly(propylene fumarate) synthesis by step polymerization of diethyl fumarate and propylene glycol using zinc chloride as a catalyst; vol. 13, No. 1; XP008085841.
International Searching Authority; form PCT/ISA/220; dated Jul. 2014.

\* cited by examiner

— Pore Dimension
— Strut Dimension
(Along space diagonal [111])

WELL-DEFINED DEGRADABLE POLY(PROPYLENE FUMARATE) POLYMERS AND SCALABLE METHODS FOR THE SYNTHESIS THEREOF

CROSS REFERENCE TO RELATED APPLICATIONS

This application claims the benefit of International Application Number PCT/US2015/061314 entitled "Well-Defined Degradable Poly(Propylene Fumarate) Polymers and Scalable Methods for the Synthesis Thereof" filed Nov. 18, 2015, which claims the benefit of U.S. provisional patent application Ser. No. 62/081,219 entitled "Products and Methods for Synthesis and Functionalization of Resorbable Materials, and use thereof as a Medical Device," filed Nov. 18, 2014, and U.S. provisional patent application Ser. No. 62/139,196 entitled "Well-Defined Degradable Poly(Propylene Fumarate) Polymers and Scalable Methods for the Synthesis Thereof," filed Mar. 27, 2015, all of which are incorporated herein by reference in their entirety.

NAMES OF THE PARTIES TO A JOINT RESEARCH AGREEMENT

The subject matter of the present application was developed pursuant to a Joint Research Agreement between The University of Akron and The Ohio State University.

FIELD OF THE INVENTION

One or more embodiments of the present invention relates to a novel poly(propylene fumarate) polymer and methods for making poly(propylene fumarate) polymers. In certain embodiments, the present invention relates to a well-defined biodegradable poly(propylene fumarate) polymer and scalable methods for making and functionalizing same. In certain embodiments, the present invention relates to a well-defined biodegradable poly(propylene fumarate) polymer for use in various regenerative medicine applications.

BACKGROUND OF THE INVENTION

Additive manufacturing, also known as three-dimensional (3D) printing, has the potential to revolutionize the way surgeons address complicated reconstructive efforts in pathogenesis, congenital deformity, senescence, oral, maxillofacial, and/or orthopedic trauma, and cancer defect repairs, just to name a few of the many possible biomedical applications for 3D printing. While numerous 3D printing methods have been reported, photocrosslinking-based printing methods in particular have shown potential for reliable, high-fidelity rendering of solid-cured polymer scaffolds that are designed to fit defects visualized by medical imaging. Advances in image projection via digital light printing (DLP) technology have enabled the 3D printing of tissue engineering scaffolds with complex geometric designs coupled with very fine (<50 µm) features.

To realize this potential, efforts have been made to develop a cost effective, non-toxic, biodegradable polymer that works well with known 3D printing technologies, including photochemical cross linking techniques. Moreover, since the idea is for these 3D printed structures to be implanted into the human body, the polymers used must withstand regulatory scrutiny. While there are many inert photocrosslinkable resins, very few are non-toxic, implantable and resorbable. Of this final category the most explored are polylactides, poly(c-caprolactone), and poly(propylene fumarate) (PPF). In regards to resorption profiles, polylactides have occasionally been found to undergo rapid bulk degradation leading to a localized acidosis and inflammation. Poly(ε-caprolactone) is known to degrade very slowly, sometimes over years, thereby limiting the necessary remodeling or vascularization of neotissues. Poly(propylene fumarate) (PPF) was developed, in part, because of a desire to have a material which has safe and controllable degradation and properties expected to be useful for such things as controlled drug release, stents, blood vessels, nerve grafts, and cartilage tissue engineering, especially bone tissue engineering. Since its invention via the step growth polymerization method more than two decades ago, PPF has been investigated with much success as scaffolding materials for skeletal repair. Subsequent reports have improved upon the synthetic methods and resulting materials.

One major factor limiting the availability of resorbable photo-cross linkable polymers such as PPF is the lack of GMP-grade materials, i.e., materials which meet Good Manufacturing Practices requirements implemented by the FDA, required to push forward into large animal models and pilot human trials. PPF is traditionally synthesized using one of a variety of step-growth condensation reactions. To date, it has not been possible to reliably and reproducibly synthesize well-defined, low-molecular-mass oligomers on the scale required for widespread 3D printing applications and commercialization. In particular, known step-growth methods of synthesizing PPF require high energy (heat) input, high vacuum, long reaction times, and result in low conversion (~35%) with uncontrolled molecular mass distribution, conjugate-addition side reactions, and unwanted cross-linking, all of which greatly influence the mechanical properties and degradation rates of the final product. Moreover, these methods are slow, labor intensive and very expensive, and, as a result, have not been found commercially viable.

Particularly problematic is the difficulty in controlling the molecular mass distribution inherent in these step-growth methods. No two batches are exactly the same. These polymers tend to have a relatively high molecular mass distribution ($Đ_m$) (also known as the Polydispersity Index (PDI)), and the colors and mechanical/viscosity properties of the polymers are inconsistent from batch to batch. This batch to batch variation has been found to lead to significant difficulty in predicting mechanical properties that influence biological performance, such as the resorption time, the evenness of resorption (due to long chains acting as a nexus in some locations and not others—i.e., uneven cross linking mesh), as well as uneven cross linking incorporation of other resins used as a solvent(s), photo-initiator(s), dye(s), pigment(s), or component(s) (e.g., diethyl fumarate (DEF), bioactive molecules) during 3D printing. The inability of researchers to reliably predict the 3D printing and subsequent biological performance of these polymers has made it very difficult to obtain the necessary regulatory approvals for use of these polymers in implants and other medical devices. In fact, it is believed that to date PPF has not been part of any FDA-approved device or therapy, despite more than two decades of continuous study of its use in regenerative medicine and successful experimental results.

More recently, PPF with a high molecular mass, a narrow $Đ_m$ (below 1.6) and low ether linkage (<1%) have been successfully synthesized using a chain growth mechanism with mild reaction conditions. In this method, maleate anhydride and epoxide are polymerized through a ring-opening copolymerization with chromium salen as a catalyst at 45° C., and the produced poly(propylene maleate) (PPM)

is then isomerized using diethylamine at room temperature for 16 hours to yield PPF. The PPF synthesized in this way was a solid and had a MW of more than 4 kDa, a molecular mass distribution of 1.6 and less than 1% ether linkage with 99% conversion. Compared with traditional synthesis methods, the chain growth mechanism provides PPF with better molecular properties and the reaction is more reproducible, making it possible to produce PPF with controlled properties for further mechanical, toxicity and degradation tests, and for large-scale production in manufacturing. Unfortunately, however, the high molecular weights, lack of flowability, and residual chromium metal of the PPF polymers made using these methods, render them unsuitable for 3D printing or other applications in regenerative medicine.

What is needed in the art is a low molecular weight, flowable, non-toxic, resorbable PPF polymer with constrained and predictable material properties and related methods for its making and use, which are suitable for 3D printing and use in medical devices and can be made inexpensively and in commercially reasonable quantities using GMP.

SUMMARY OF THE INVENTION

One or more embodiments of the present invention provide a low molecular weight, non-toxic, resorbable PPF polymer (and related methods for its making and use) having constrained and predictable material properties suitable for 3D printing, which can be made inexpensively in commercially reasonable quantities.

In a first aspect, the present invention provides a poly(propylene fumarate) polymer for use in 3D printing having a number average molecular weight ($M_n$) of from about 450 Daltons to about 3500 Daltons and a molecular mass distribution ($Đ_m$) of from 1.0 to 2.0. In some embodiments, present invention is directed to the poly(propylene fumarate) polymer of the first aspect of the present invention wherein the said number average molecular weight ($M_n$) is from about 700 to about 3200. In one or more embodiments, the poly(propylene fumarate) polymer of the present invention includes any one or more of the above referenced embodiments of the first aspect of the present invention having a glass transition temperature ($T_g$) of from about −25° C. to about 12°C. In one or more embodiments, the poly(propylene fumarate) polymer of the present invention includes any one or more of the above referenced embodiments of the first aspect of the present invention having a peak number average molecular mass ($M_p$ of from about 980 Daltons to about 5900 Daltons.

In one or more embodiments, the poly(propylene fumarate) polymer of the present invention includes any one or more of the above referenced embodiments of the first aspect of the present invention having an intrinsic viscosity of from about 0.025 dL/g to about 0.078 dL/g. In one or more embodiments, the poly(propylene fumarate) polymer of the present invention includes any one or more of the above referenced embodiments of the first aspect of the present invention, wherein said poly(propylene fumarate) polymer contains less than 1% w/w of poly(maleic anhydride-co-propylene oxide) polymer chains. In one or more embodiments, the poly(propylene fumarate) polymer of the present invention includes any one or more of the above referenced embodiments of the first aspect of the present invention, wherein said poly(propylene fumarate) polymer does not contain poly(maleic anhydride-co-propylene oxide) polymer chains.

In one or more embodiments, the poly(propylene fumarate) polymer of the present invention includes any one or more of the above referenced embodiments of the first aspect of the present invention, having the formula:

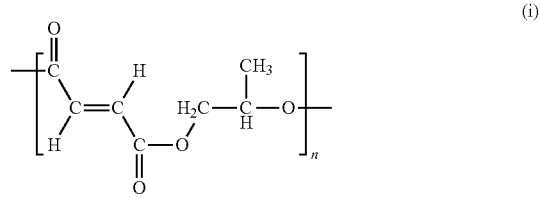

(i)

wherein n is an integer from 3 to 30.

In a second aspect, the present invention provides a method for making a poly(propylene fumarate) polymer for use in 3D printing comprising: dissolving maleic anhydride and propylene oxide in a suitable solvent under an inert atmosphere; adding a suitable initiator; heating the mixture to a temperature of from about 60° C. to about 120° C. for a period of from about 0.5 hours to about 100 hours to produce a poly(maleic anhydride-co-propylene oxide); collecting and purifying the poly(maleic anhydride-co-propylene oxide)polymer; dissolving the poly(maleic anhydride-co-propylene oxide) in a suitable solvent and adding a catalyst; heating the mixture to a temperature of from about 5° C. to about 80° C. for a period of from about 5 hours to about 100 hours to produce a poly(propylene fumarate) polymer.

In some embodiments, present invention is directed to the method for making a poly(propylene fumarate) polymer of the second aspect of the present invention method of claim 9 wherein the solvent used to dissolve the maleic anhydride and propylene oxide is selected from the group consisting of toluene, tetrahydrofuran (THF), dioxane, and combinations thereof. In one or more embodiments, the method for making a poly(propylene fumarate) polymer of the present invention includes any one or more of the above referenced embodiments of the second aspect of the present invention, wherein the solvent used to dissolve the maleic anhydride and propylene oxide is toluene.

In one or more embodiments, the method for making a poly(propylene fumarate) polymer of the present invention includes any one or more of the above referenced embodiments of the second aspect of the present invention, wherein the initiator is magnesium ethoxide (Mg(OEt)$_2$). In one or more embodiments, the method for making a poly(propylene fumarate) polymer of the present invention includes any one or more of the above referenced embodiments of the second aspect of the present invention, wherein the molar ratio of either the maleic anhydride or the propylene oxide to the initiator is from about 3:1 to about 400:1.

In one or more embodiments, the method for making a poly(propylene fumarate) polymer of the present invention includes any one or more of the above referenced embodiments of the second aspect of the present invention, further comprising cooling the reaction mixture under an inert gas atmosphere; evaporating the volatile compounds from the mixture by distillation or reduced pressure; adding chloroform or dichloromethane; washing the solution with an aqueous solution, thereby forming an organic layer containing the poly(maleic anhydride-co-propylene oxide) polymer intermediate and an aqueous layer; collecting and pouring this organic layer into a non-polar organic solvent such as hexane to cause the poly(maleic anhydride-co-propylene oxide) polymer to precipitate; collecting the poly(maleic anhydride-co-propylene oxide); dissolving the poly(maleic anhydride-co-propylene oxide) polymer in a small amount of a suitable solvent; concentrating the solution by evaporation; and drying the concentrated solution under a vacuum, to produce a purified poly(maleic anhydride-co-propylene oxide) polymer intermediate. In one or more embodiments, the method for making a poly(propylene fumarate) polymer of the present invention includes any one or more of the above referenced embodiments of the second aspect of the present invention, wherein the inert atmosphere comprises nitrogen.

In one or more embodiments, the method for making a poly(propylene fumarate) polymer of the present invention includes any one or more of the above referenced embodiments of the second aspect of the present invention, wherein the volatile compounds are evaporated from the mixture by distillation or reduced pressure. In one or more embodiments, the method for making a poly(propylene fumarate) polymer of the present invention includes any one or more of the above referenced embodiments of the second aspect of the present invention, wherein the poly(maleic anhydride-co-propylene oxide) polymer is collected by separatory funnel.

In one or more embodiments, the method for making a poly(propylene fumarate) polymer of the present invention includes any one or more of the above referenced embodiments of the second aspect of the present invention, wherein the suitable solvent comprises chloroform or dichloromethane.

In one or more embodiments, the method for making a poly(propylene fumarate) polymer of the present invention includes any one or more of the above referenced embodiments of the second aspect of the present invention, wherein the solvent of used to dissolve the poly(maleic anhydride-co-propylene oxide) polymer intermediate is selected from the group consisting of chloroform, tetrahydrofuran (THF), dioxane, and combinations thereof. In one or more embodiments, the method for making a poly(propylene fumarate) polymer of the present invention includes any one or more of the above referenced embodiments of the second aspect of the present invention, wherein the solvent used to dissolve the poly(maleic anhydride-co-propylene oxide) polymer intermediate is chloroform. In one or more embodiments, the method for making a poly(propylene fumarate) polymer of the present invention includes any one or more of the above referenced embodiments of the second aspect of the present invention, wherein the catalyst is diethylamine.

In one or more embodiments, the method for making a poly(propylene fumarate) polymer of the present invention includes any one or more of the above referenced embodiments of the second aspect of the present invention, further comprising collecting and purifying the poly(propylene fumarate) polymer. In one or more embodiments, the method for making a poly(propylene fumarate) polymer of the present invention includes any one or more of the above referenced embodiments of the second aspect of the present invention, wherein the step of collecting and purifying the poly(propylene fumarate) polymer comprises: concentrating the dissolved poly(propylene fumarate) polymer intermediate by evaporation; washing the resulting solution with a buffered aqueous solution to remove the catalyst, thereby forming an forming an organic layer and an aqueous layer; collecting the organic layer; concentrating the organic layer by evaporation; adding sodium sulfate or any other inorganic drying agent, acidic proton or molecular sieve to remove remaining water; filtering out the sodium sulfate or other inorganic drying agent or molecular sieve; pouring the resulting mixture into a non-polar organic solvent to cause the poly(propylene fumarate) polymer to precipitate; collecting the poly(propylene fumarate) polymer and drying it under a vacuum, to produce a purified poly(propylene fumarate) polymer.

In one or more embodiments, the method for making a poly(propylene fumarate) polymer of the present invention includes any one or more of the above referenced embodiments of the second aspect of the present invention, wherein the dissolved poly(maleic anhydride-co-propylene oxide) polymer intermediate is concentrated by rotary evaporation or reduced pressure. In one or more embodiments, the method for making a poly(propylene fumarate) polymer of the present invention includes any one or more of the above referenced embodiments of the second aspect of the present invention, wherein the buffered aqueous solution comprises a phosphate buffered saline solution.

In one or more embodiments, the method for making a poly(propylene fumarate) polymer of the present invention includes any one or more of the above referenced embodiments of the second aspect of the present invention, wherein the organic layer containing the water washed polymer is collected by separatory funnel. In one or more embodiments, the method for making a poly(propylene fumarate) polymer of the present invention includes any one or more of the above referenced embodiments of the second aspect of the present invention, wherein the organic layer the organic layer containing the water washed polymer is concentrated by rotary evaporation or reduced pressure. In one or more embodiments, the method for making a poly(propylene fumarate) polymer of the present invention includes any one or more of the above referenced embodiments of the second aspect of the present invention, wherein non-polar organic solvent used to precipitate the poly(propylene fumarate) polymer comprises hexane.

BRIEF DESCRIPTION OF THE DRAWINGS

For a more complete understanding of the features and advantages of the present invention, reference is now made to the detailed description of the invention along with the accompanying figures in which:

FIGS. 6A and 6B are a bright field image (FIG. 6A) and a flourence image (FIG. 6B) of a direct contact assay showing the PPF polymer on a hMSC monolayer. FIGS. 6C and 6D are a bright field image (FIG. 6C) and a flourence image (FIG. 6D) of a direct contact assay showing hMSCs cultured onto the PPF polymer material. It should be understood that the lighter areas in FIGS. 6B and 6D are the areas that fluoresced green in the color image. Scale bar=500 µm.

FIG. 16B is an enlargement of the PPF scaffold shown in FIG. 16A.

DETAILED DESCRIPTION OF THE ILLUSTRATIVE EMBODIMENTS

Figure 1:
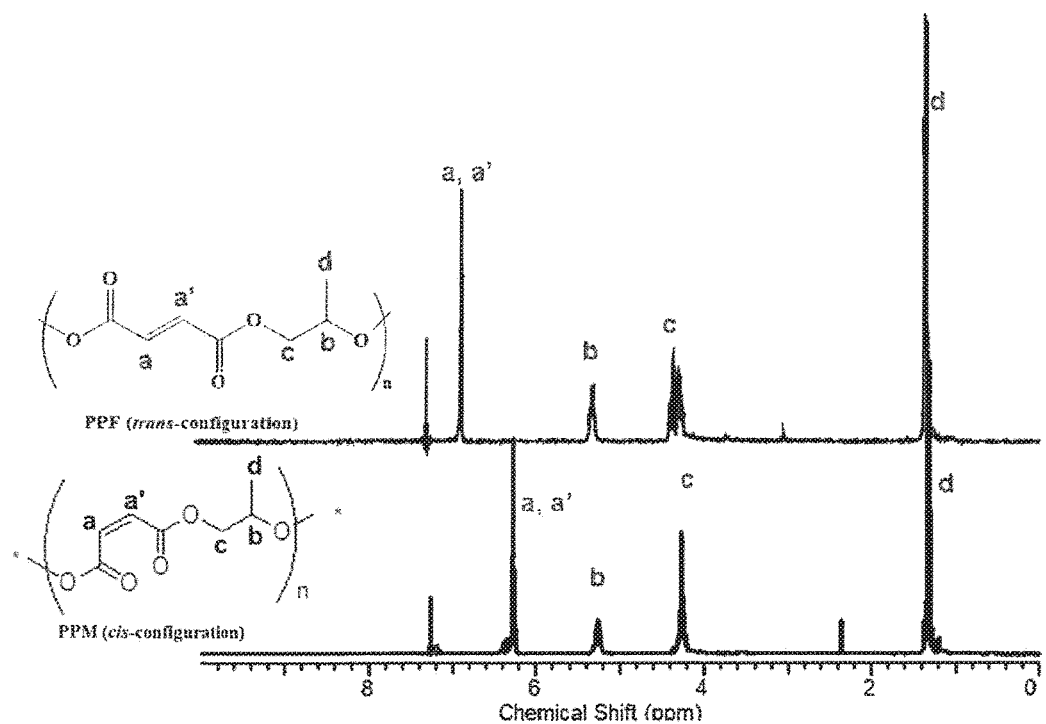
FIG. 1 is a schematic comparing the $^1$H NMR spectra ($CDCl_3$, 300 MHz) for a PPM intermediate (bottom) and PPF polymer (top) according to one or more embodiments of the present invention, indicating quantitative conversion of the cis stereochemistry (PPM intermediate) to the trans configuration (PPF polymer).

One or more embodiments of the present invention provide a low molecular weight, non-toxic, resorbable PPF polymer (and related methods for its making and use) having a well-defined molecular mass and molecular mass distribution as well as predictable viscosity properties, that is suitable for 3D printing and can be made inexpensively in commercially reasonable quantities. These PPF polymers afford predictable and reliable mechanical performance and resorption profiles may also reduce the amount of solvent necessary to insure sufficient flow of material during 3D printing. MALDI mass spectrometry show precisely the end group fidelity and size exclusion chromatography (SEC) demonstrates number average molecular mass distributions (<1.6) of a series of low molecular mass ($M_n$=700-3000 Da) oligomers. In one or more embodiments, the corresponding intrinsic viscosities range from 0.0288±0.0009 dL/g to 0.0780±0.0022 dL/g. Further, standardized ISO 10993-5 testing has shown that materials 3D printed from the PPF polymers of embodiments of the present invention are non-toxic to both L929 mouse fibroblasts and human mesenchymal stem cells.

In a first aspect, the present invention is directed to a novel low molecular weight resorbable PPF polymer having a low molecular mass distribution ($Đ_m$) and a wide variety of potential uses, particularly as a component in resins for 3D printing. The PPF polymers of the present invention are not toxic and can be used in tissue scaffolds and other medical devices that are implanted within a human body or other living organism. Moreover, the PPF polymer is both degradable and resorbable. The polymer is degradable or biodegradable in that it will break down in vivo into its component parts within a time frame suitable for therapeutic purposes. The rate of degradation for a particular PPF polymer according to embodiments of the present invention will depend upon its molecular weight, cross linking density, and geometric considerations (e.g., relative amount of surface area) of the traditionally formed or 3D printed material. The PPF polymer of embodiments of the present invention is also resorbable in that its degradation products are well tolerated by the body and may be either metabolized by the body or excreted within a time frame suitable for therapeutic purposes. In the case of the PPF polymers according to embodiments of the present invention, the degradation products are fumaric acid (a normal metabolic product) and 1,2-propanediol, which is a common diluent in drug formulations and is excreted by the body.

The structure of the PPF polymers of the present invention was confirmed by proton Nuclear Magnetic Resonance spectroscopy ($^1$H NMR) and carbon 13 Nuclear Magnetic Resonance spectroscopy ($^{13}$C NMR). (See FIGS. 1 and 2) In some embodiments, the PPF polymers of the present invention have the formula:

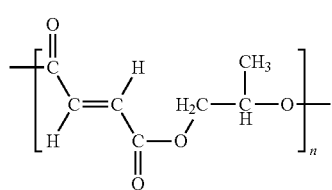

(i)

wherein "n" is an integer from 3 to 30. In some embodiments, n may be an integer from 5 to 30. In some embodiments, n may be an integer from 15 to 30. In some embodiments, n may be an integer from 3 to 25. In some embodiments, n may be an integer from 3 to 20. In some embodiments, n may be an integer from 3 to 15. In some embodiments, n may be an integer from 5 to 15. In some embodiments, n may be an integer from 3 to 10. In some embodiments, n may be an integer from 3 to 6.

The molecular mass and mass distribution properties of PPF polymers according to various embodiments of the present invention were characterized by Size Exclusion Chromatography (SEC). In one or more embodiments, the PPF polymer (i) will have a number average molecular mass ($M_n$) of from about 450 Da to about 3500 Da. In some embodiments, the PPF polymer may have a $M_n$ of from about 500 Da to about 3000 Da. In some embodiments, the PPF polymer may have a $M_n$ of from about 750 Da to about 2500 Da. In some embodiments, the PPF polymer may have a $M_n$ of from about 1000 Da to about 2000 Da. In some embodiments, the PPF polymer may have a $M_n$ of from about 1000 Da to about 1500 Da. In some embodiments, the PPF polymer may have a $M_n$ of from about 450 Da to about 1000 Da. In some embodiments, the PPF polymer may have a $M_n$ of from about 1000 Da to about 3500 Da. In some embodiments, the PPF polymer may have a $M_n$ of from about 1500 Da to about 3500 Da. In some embodiments, the PPF polymer may have a $M_n$ of from about 2000 Da to about 3000 Da.

In some embodiments, the PPF polymer may have a $M_n$ of about 700 Da ($M_p$: 980 Da). In some embodiments, the PPF polymer may have a $M_n$ of about 1269 Da ($M_p$: 1711 Da). In some embodiments, the PPF polymer may have a $M_n$ of about 1362 Da. In some embodiments, the PPF polymer may have a $M_n$ of about 1856 Da ($M_p$: 2573 Da). In some embodiments, the PPF polymer may have a $M_n$ of about 2367 Da ($M_p$: 3190 Da). In some embodiments, the PPF polymer may have a $M_n$ of about 3200 Da ($M_p$: 5974 Da). In some embodiments, the PPF polymer may have a $M_n$ of about 1496 Da.

In one or more embodiment of the present invention, the PPF polymer will have a weight average molecular mass ($M_w$) of from about 450 Daltons to 3500 Daltons. In one or more embodiment of the present invention, the PPF polymer will have a weight average molecular mass ($M_w$) of from about 900 Daltons to 7000 Daltons. In one or more embodiment of the present invention, the PPF polymer will have a weight average molecular mass ($M_w$) of from about 1000 Daltons to 1500 Daltons. In one or more embodiment of the present invention, the PPF polymer will have a weight average molecular mass ($M_w$) of from about 1000 Daltons to 2000 Daltons. In one or more embodiment of the present invention, the PPF polymer will have a weight average molecular mass ($M_w$) of from about 1000 Daltons to 3000 Daltons. In one or more embodiment of the present invention, the PPF polymer will have a weight average molecular mass ($M_w$) of from about 2000 Daltons to 3000 Daltons. In one or more embodiment of the present invention, the PPF polymer will have a weight average molecular mass ($M_w$) of from about 2000 Daltons to 4000 Daltons. In one or more embodiment of the present invention, the PPF polymer will have a weight average molecular mass ($M_w$) of from about 2000 Daltons to 6000 Daltons.

As set forth above, the PPF polymers according to embodiments of the present invention also have a well-defined and relatively low molecular mass distribution ($Đ_m$), which may be defined as is the ratio of $M_w$ to the $M_n$. As used herein, the term "well-defined" as applied to the molecular mass distribution means a of 2.0 or less. In some embodiments, the PPF polymer will have a $Đ_m$ of from about 1.0 to about 2.0. In some embodiments, the PPF polymer will have a $Đ_m$ of from about 1.0 to about 1.8. In some embodiments, the PPF polymer will have a $Đ_m$ of from about 1.0 to about 1.6. In some embodiments, the PPF polymer will have a $Đ_m$ of from about 1.0 to about 1.4. In some embodiments, the PPF polymer will have a $Đ_m$ of from about 1.0 to about 1.2.

In some embodiments, the PPF polymer has a $Đ_m$ of about 1.35. In some embodiments, the PPF polymer has a $Đ_m$ of about 1.57. In some embodiments, the PPF polymer has a $Đ_m$ of about 1.78. In some embodiments, the PPF polymer has a $Đ_m$ of about 1.46. In some embodiments, the PPF polymer has a $Đ_m$ of about 1.64. In some embodiments, the PPF polymer has a $Đ_m$ of about 1.50. In some embodiments, the PPF polymer has a $Đ_m$ of about 1.60. In some embodiments, the PPF polymer has a $Đ_m$ of about 1.70.

Figure 3:
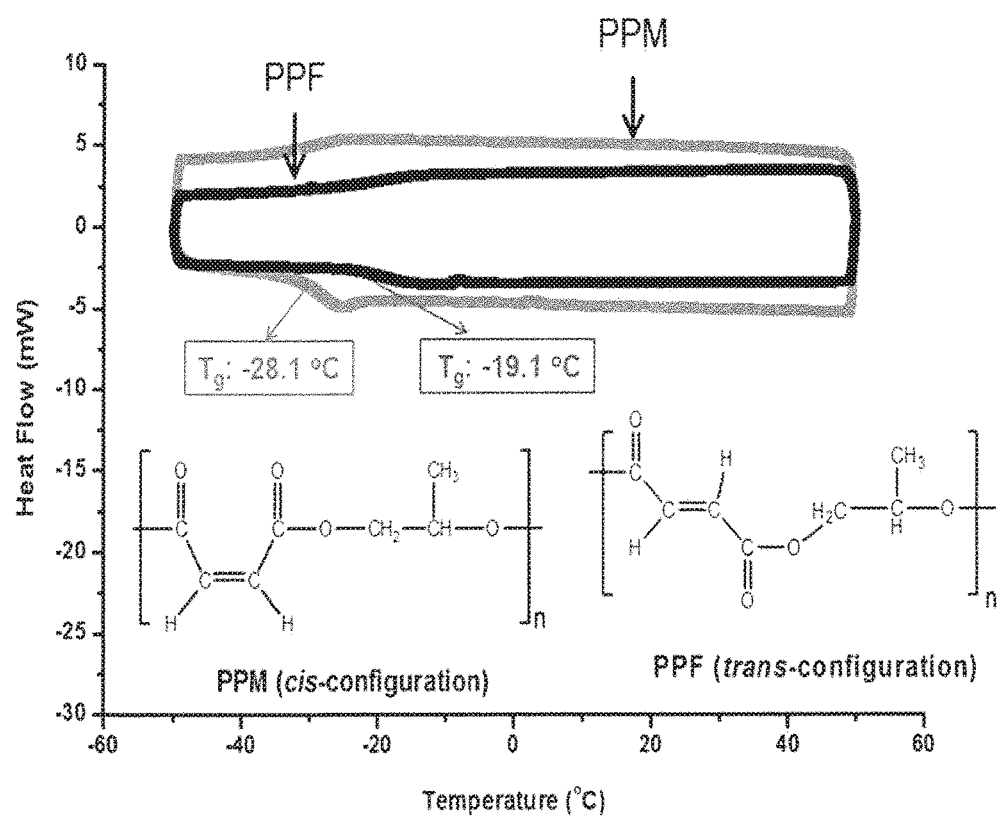
FIG. 3 a schematic comparing Differential Scanning calorimetry (DSC) characterizations (−50° C.-50° C., 10° C./min) for a PPM intermediate and PPF polymer according to one or more embodiments of the present invention.

As will be appreciated by those of skill in the art, the PPF polymers of the present invention will have a glass transition temperature ($T_g$). (See also, FIG. 3). The $T_g$ of polymers according to embodiments of the present invention is not particularly limited. In some embodiments, the $T_g$ of the PPF polymer may be from −30° C. to 20° C. In some embodiments, the $T_g$ of the PPF polymer may be from −25° C. to 12° C. In some embodiments, the $T_g$ of the PPF polymer may be from −10° C. to 5° C. In some embodiments, the $T_g$ of the PPF polymer may be −25° C. In some embodiments, the $T_g$ of the PPF polymer may be −19° C. In some embodiments, the $T_g$ of the PPF polymer may be −3° C. In some embodiments, the $T_g$ of the PPF polymer may be 3° C.

In some embodiments, the PPF may have a $M_n$ of 700 Da, $Đ_m$ of 1.6, and $T_g$ of −25° C. In some embodiments, the PPF may have a $M_n$ of 1270 Da, $Đ_m$ of 1.5, and $T_g$ of −3° C. In some embodiments, the PPF may have a $M_n$ of 1860 Da, $Đ_m$ of 1.6, and $T_g$ of 0° C. In some embodiments, the PPF may have a $M_n$ of 2450 Da, $Đ_m$ of 1.6, and $T_g$ of 6° C. In some embodiments, the PPF may have a $M_n$ of 3200 Da, $Đ_m$ of 1.7, and $T_g$ of 12° C.

Figure 4A:
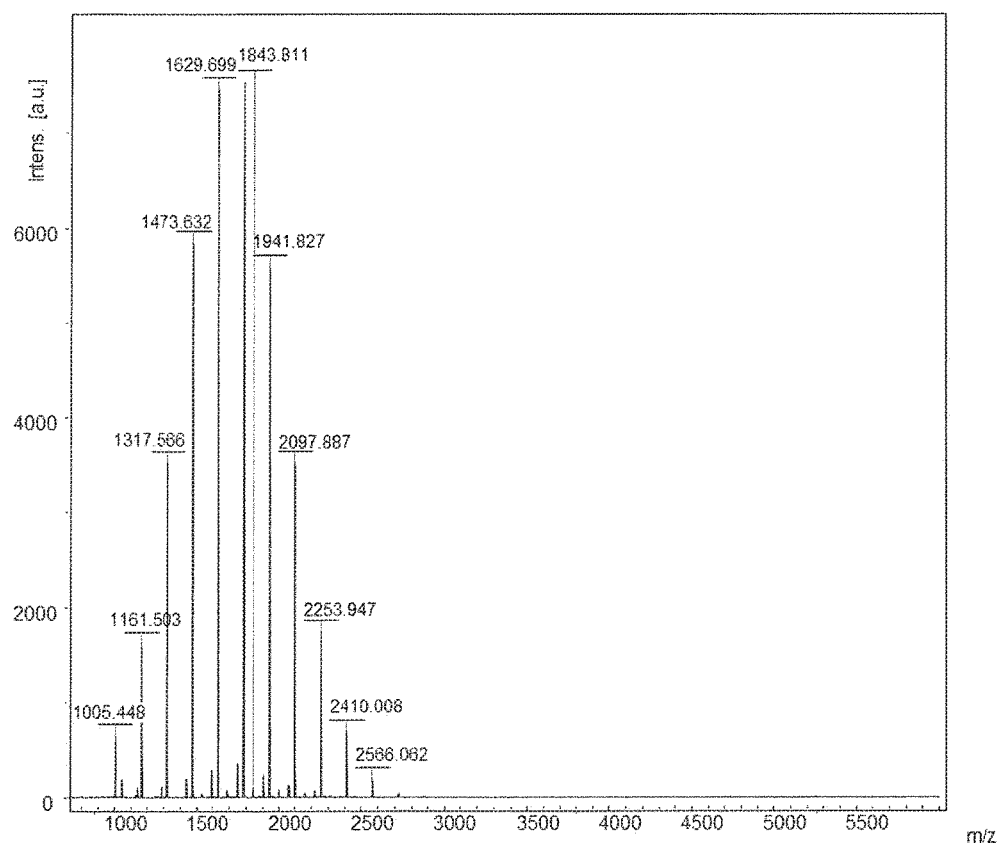
FIG. 4A is a MALDI-TOF mass spectrograph of PPF sample number 3 in Table 1 showing mass distribution in this sample.
Figure 4B:
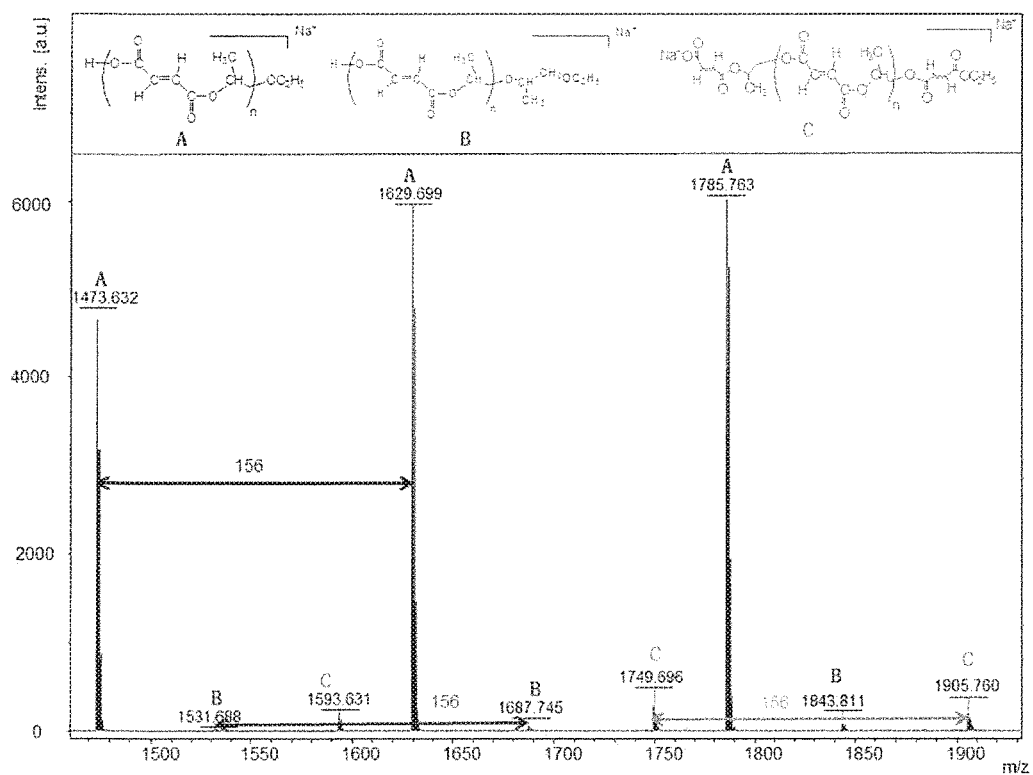
FIG. 4B is an enlarged portion of a MALDI-TOF mass spectrograph of PPF sample number 3 in Table 1 showing the repeat unit in PPF and the possible end group chemistries which correspond the individual peaks in the distribution depicted in the mass spectrometry data.
Figure 5A:
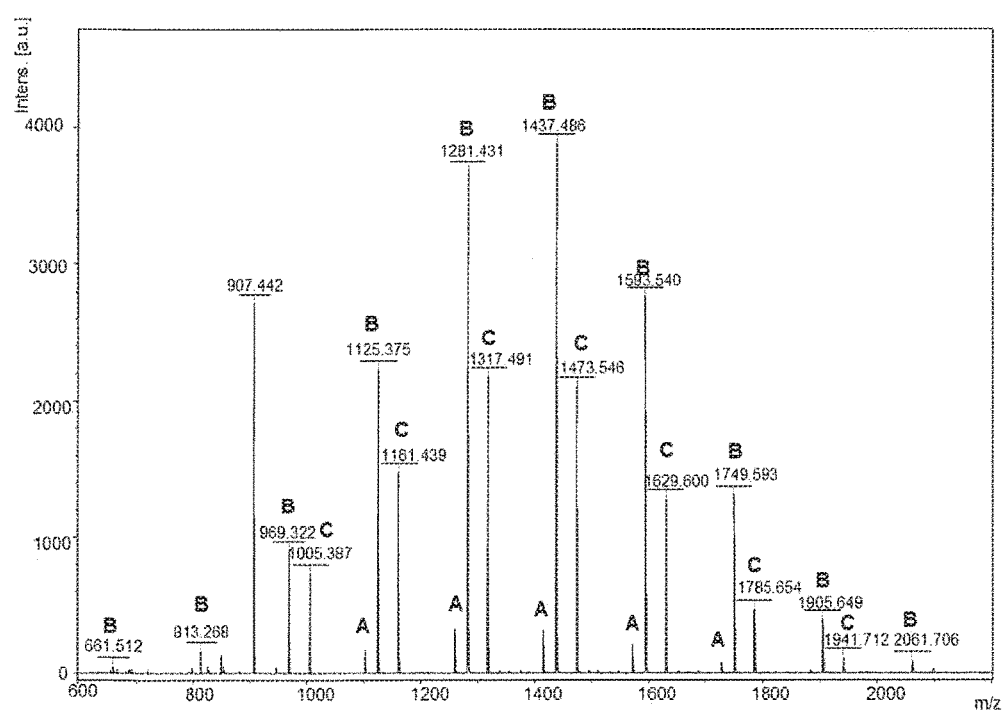
FIG. 5A is a MALDI-TOF mass spectrograph of PPF sample number 2 in Table 1 showing mass distribution in this sample.
Figure 5B:
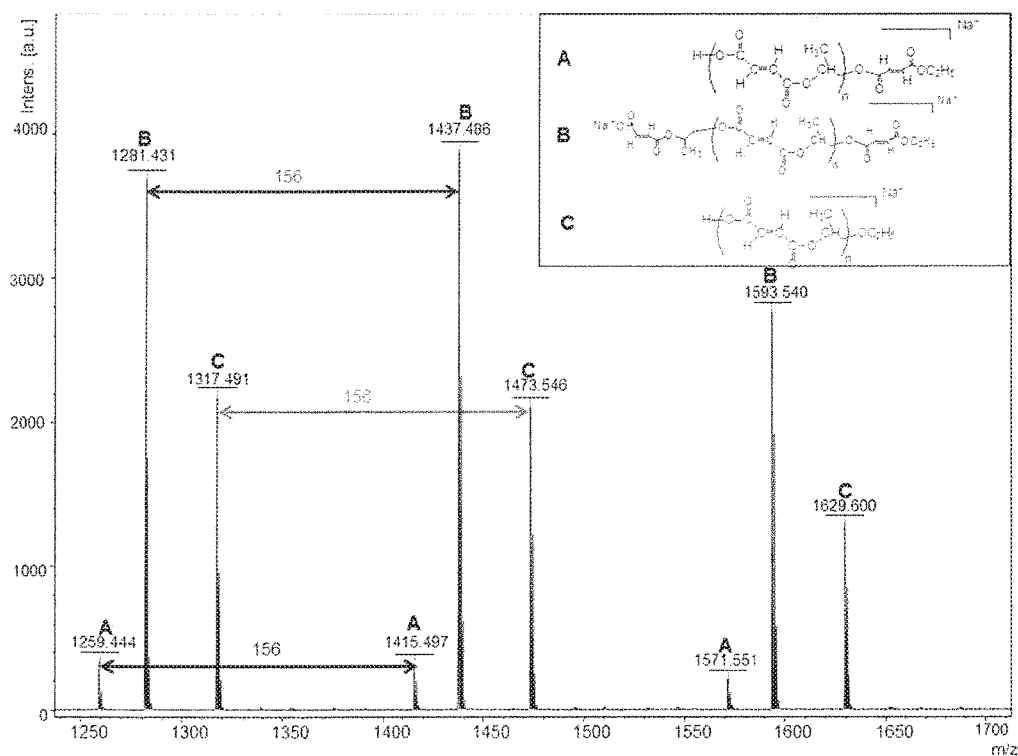
FIG. 5B is an enlarged portion of a MALDI-TOF mass spectrograph of PPF sample number 2 in Table 1 showing the repeat unit in PPF and the possible end group chemistries which correspond the individual peaks in the distribution depicted in the mass spectrometry data.
Figure 6A:
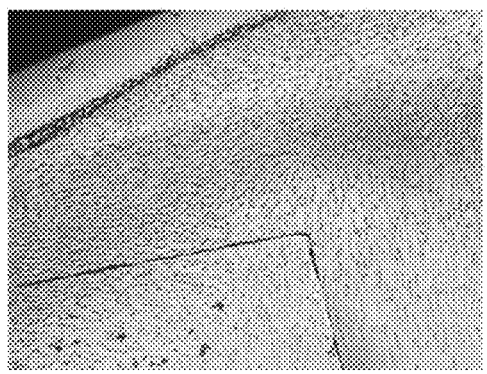
FIGS. 6A-D are images showing the results of cytotoxicity experiments to confirm the in vitro biocompatibility of a PPF according to one embodiment of the present invention with human bone marrow-derived mesenchymal stem cells (RoosterBio, Frederick, Md.) (hMSC).
Figure 6B:
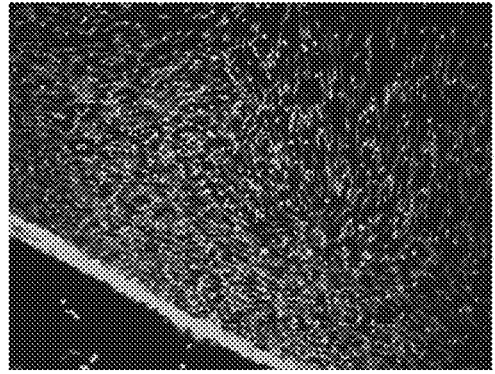
Figure 6C:
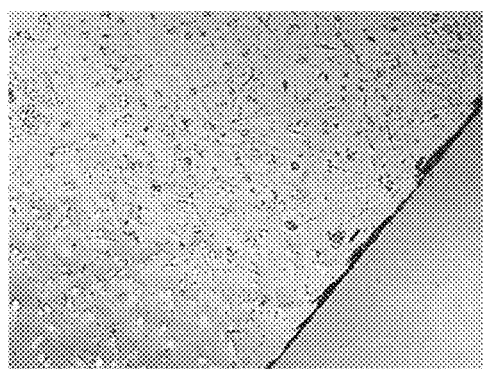
Figure 6D:

In some embodiments, the PPF polymers of the present invention have the characteristics set forth in Table 1, below.

spond to the individual peaks in the mass spectrometry data. As seen in FIG. 4B, there are three groups (labeled with A, B, C) of possible end groups in this sample (PPF sample number 3 in Table 1). The m/z=156 between two adjacent peaks shows the mass of repeat unit, which equals to the mass of maleic anhydride and propylene oxide. The predominate end group population is an ethoxy group (A). These characteristics support the successful synthesis of PPF. FIG. 5A is a MALDI-TOF mass spectrograph of PPF sample number 2 in Table 1 showing mass distribution in this sample and FIG. 5B is an enlarged portion of a MALDI-TOF mass spectrograph of PPF sample number 2 in Table 1 showing the repeat unit in PPF and the possible end group chemistries which correspond the individual peaks in the distribution depicted in the mass spectrometry data.

As set forth above, at ambient temperature the PPF polymers of embodiments of the present invention are a viscous fluid. These polymers, however, may be cross linked using any suitable method known in the art for that purpose to form a solid having known mechanical properties. Suitable means for cross linking the PPF polymers of embodiments of the present invention include, but are not limited to radical initiated photo-cross linking. In some embodiments,

TABLE 1

Polymer Data with Temperature, Time, Ratios $M_w$, $M_p$, $M_n$, $T_g$, and Intrinsic Viscosity

| PPF | MAn or PO (mol) | C (mol/L) | Molar ratio of Monomer/Mg(OEt)$_2$ | Time (h) | Temp. (° C.) | Molar ratio of PPM/DEA | Temp (° C.) | Time (h) | Yield (%) | $M_n$ (Da) | $Đ_m$ | $T_g$ (° C.) | [η] (dL/g) |
|---|---|---|---|---|---|---|---|---|---|---|---|---|---|
| 1 | 6.962 | 7.14 | 5.7 | 6 | r.t. | 6.67 | 50 | 16 | 51 | 700 | 1.6 | −25 | 0.0288 ± 0.0009 |
| 2 | 2.856 | 7.14 | 24 | 40 | 80 | 6.67 | 60 | 16 | 65 | 1270 | 1.5 | −3 | 0.0490 ± 0.0001 |
| 3 | 2.856 | 7.14 | 48 | 40 | 80 | 10 | 60 | 24 | 48 | 1860 | 1.6 | 0 | 0.0529 ± 0.0013 |
| 4 | 2.856 | 7.14 | 200 | 42 | 80 | 10 | 60 | 22 | NA | 2450 | 1.6 | 6 | 0.0622 ± 0.0006 |
| 5 | 0.714 | 7.14 | 200 | 138 | 80 | 6.67 | 55 | 20 | NA | 3160 | 1.7 | 12 | 0.0780 ± 0.0022 |

At ambient temperature, the PPF polymers of embodiments of the present invention are a viscous fluid and may further be described in terms of intrinsic viscosity. (See Table 1, above) The intrinsic viscosity is measured herein in THF using an Ubbelohde viscometer at 35° C.

In some embodiments, the PPF polymer has an intrinsic viscosity of from about 0.025 dL/g to about 0.090 dL/g. In some embodiments, the PPF polymer has an intrinsic viscosity of from about 0.049 dL/g to about 0.078 dL/g. In some embodiments, the PPF polymer has an intrinsic viscosity of from about 0.0520 dL/g to about 0.0630 dL/g. In some embodiments, the PPF polymer has an intrinsic viscosity of about 0.0288 dL/g. In some embodiments, the PPF polymer has an intrinsic viscosity of about 0.0490 dL/g. In some embodiments, the PPF polymer has an intrinsic viscosity of about 0.0529 dL/g. In some embodiments, the PPF polymer has an intrinsic viscosity of about 0.0622 dL/g. In some embodiments, the PPF polymer has an intrinsic viscosity of about 0.0780 dL/g.

Matrix Assisted Laser Desorption/Ionization—Time-of-Flight (MALDI-TOF) mass spectroscopy is able to determine precisely the mass of the individual materials and the end group populations. At low molecular mass, MALDI is able to determine the molecular mass more precisely that size exclusion chromatography. FIG. 4A is a MALDI-TOF mass spectrograph of PPF sample number 3 in Table 1 showing mass distribution in this sample. FIG. 4B is an enlarged portion of the MALDI-TOF mass spectrograph of PPF sample number 3 in Table 1 showing the repeat unit in PPF and the possible end group chemistries which correit may be cross linked to form 3D shapes using conventional fabrication techniques, such as molds, electrospinning, or CNC, in addition to 3D printing methods such as photo cross linking, in situ heat cross linking, FDM (fused deposition modeling), laser sintering, or bioprinting. (See Examples 10, 12, and 13, below) These cross linked PPF polymers are degradable and resorbable and may be suitable for use in surgical implants and other implantable medical devices. Cellular toxicity tests conducted on cross linked PPF polymers according to embodiments of the present invention indicate that these polymers are not toxic. (See Examples 16-20; FIGS. 6A-D)

In another aspect, the present invention is directed to a novel method of synthesizing PPF polymers, such as those described above. The present novel method permits production of large quantities of low molecular weight PPF polymer suitable for traditional forming, use as an injectable, or 3D printing and implantation, among other things, without the problems identified above with respect to known PPF polymers. And while the novel method of synthesizing PPF polymers described herein may, in some embodiments, be used to synthesize the PPF polymers described above, in some other embodiments the method may be used to synthesize much larger PPF polymers. It is believed that the method of various embodiments the claimed invention may be used to synthesize PPF polymers with a $M_n$ as large as 10,000 Da.

In some embodiments, this novel method is directed to synthesizing PPF polymers using the two step process shown in Scheme 1, below.

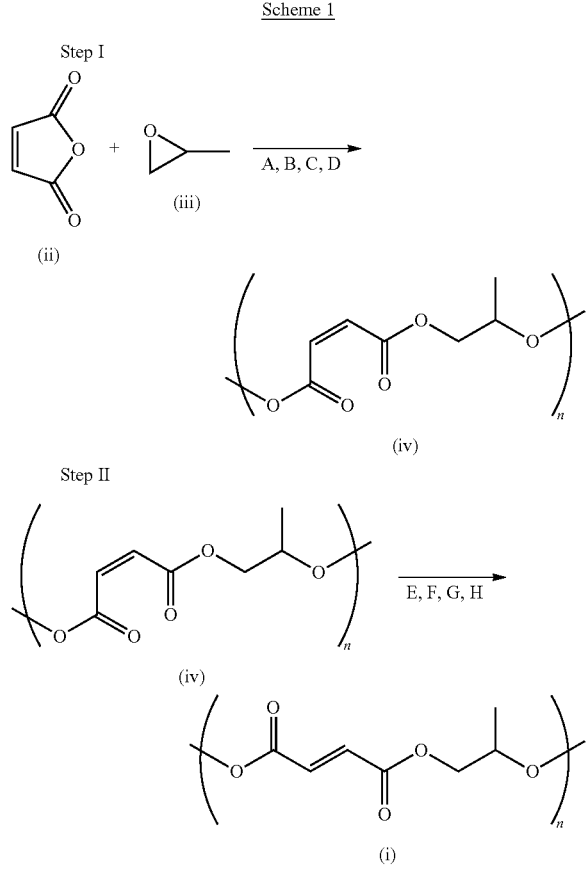

Scheme 1 wherein A and E are one or more initiator (A) or catalyst (E), B and F are each one or more solvent, C and G are each a reaction temperature, D and H are each a reaction time, and n is the number of repeating maleic anhydride-co-propylene oxide (propylene maleate) units (Step I) or propylene fumarate units (Step II).

In some embodiments, n is an integer from 3 to 90. In some embodiments, n is an integer from 3 to 30. In some embodiments, n is an integer from 3 to 20. In some embodiments, n is an integer from 3 to 10. In some embodiments, n may be an integer from 5 to 30. In some embodiments, n may be an integer from 15 to 30. In some embodiments, n may be an integer from 3 to 25. In some embodiments, n may be an integer from 3 to 20. In some embodiments, n may be an integer from 3 to 15. In some embodiments, n may be an integer from 5 to 15. In some embodiments, n may be an integer from 3 to 6.

In Step I, maleic anhydride (MAn) (ii) is reacted with propylene oxide (PO) (iii) in the presence of an initiator A and one or more solvents B, at a reaction temperature C for a reaction time D, to form the poly(maleic anhydride-co-propylene oxide (also known as poly(propylene maleate)) (PPM) intermediary (iv). As will be apparent to those of ordinary skill in the art, PPM is the cis-isomer of PPF (i). In Step II, the PPM polymer (iv) is isomerized to form the trans-isomer (PPF) (i) in the presence of a catalyst E and one or more solvents F, at a reaction temperature G for a reaction time H.

The term isomerization is used herein to refer to a reaction that converts the cis-isomer (PPM) (iv) to the trans-isomer (PPF) (i) form in the presence of a catalyst. While the isomerization step (Step II) does result in some other changes to the polymer, it should be apparent that most general aspects of the PPF polymers (i) of embodiments of the present invention, such as the approximate $M_n$, $Đ_m$, and $T_g$ ranges, are determined in the first reaction (Step I).

Turning now to the embodiment shown in Step I of Scheme 1 above, the starting materials for the reaction are MAn (ii) and PO (iii). While other embodiments are possible, it has been found that the MAn (ii) and PO (iii) of Step I react in a 1:1 molar ratio.

The reaction shown in Step I further requires one or more initiator A. While other embodiments are possible, A is preferably magnesium ethoxide ($Mg(OEt)_2$). Magnesium ethoxide has the advantage of degrading into magnesium oxide MgO and ethanol, which are generally considered to be non-toxic in this context. As will be clear to those of ordinary skill in the art, the molar ratio of monomer to initiator also plays an important role in the nature and kinetics of the reaction. Table 2 below shows $M_n$, $M_p$ and $Đ_m$ results for PPM polymers made according to the reaction of Step I above at reaction times of 3, 6, 12, 24, and 48 hours using molar ratios of monomer to initiator of 100:1, 200:1, and 300:1. (7.14 mol MAn/1 L Toluene, 80° C.) (See also FIG. 7)

TABLE 2

| Monomer to Initiator Ratio (Molar) | time (h) | Average $M_n$ (Da) | STDEV of $M_n$ (Da) | Average $M_p$ (Da) | STDEV of $M_p$ (Da) | Average $Đ_m$ | STDEV of $Đ_m$ |
|---|---|---|---|---|---|---|---|
| 100:1 | 3 | 550 | 40 | 1020 | 260 | 1.65 | 0.13 |
|  | 6 | 720 | 90 | 1300 | 390 | 1.58 | 0.02 |
|  | 12 | 990 | 40 | 1850 | 560 | 1.64 | 0.03 |
|  | 24 | 1570 | 80 | 2780 | 840 | 1.66 | 0.19 |
|  | 48 | 2100 | 250 | 2760 | 280 | 1.66 | 0.14 |
| 200:1 | 3 | 520 | 70 | 870 | 120 | 1.53 | 0.12 |
|  | 6 | 600 | 30 | 840 | 150 | 1.71 | 0.34 |
|  | 12 | 860 | 50 | 1930 | 240 | 1.72 | 0.2 |
|  | 24 | 1360 | 140 | 3040 | 400 | 1.7 | 0.23 |
|  | 48 | 2740 | 180 | 3890 | 870 | 1.67 | 0.14 |
| 300:1 | 3 | 480 | 30 | 810 | 80 | 1.48 | 0.11 |
|  | 6 | 640 | 40 | 1050 | 60 | 1.42 | 0.02 |
|  | 12 | 860 | 50 | 1560 | 60 | 1.5 | 0.05 |
|  | 24 | 1200 | 180 | 2420 | 290 | 1.62 | 0.03 |
|  | 48 | 2060 | 490 | 3930 | 700 | 1.62 | 0.02 |

Figure 7:
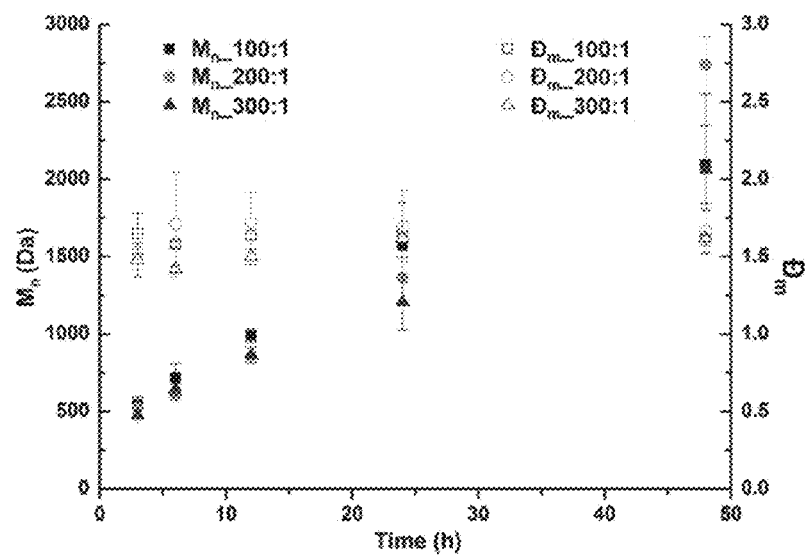
FIG. 7 is a kinetic plot showing near linear growth of molecular mass with time. Number average molecular weight ($M_n$), and molecular mass distribution ($Đ_m$) are shown as a function of reaction time for PPM intermediates made according to one or more embodiments of the present invention using molar ratios of monomer to initiator of 100:1, 200:1, and 300:1.

In FIG. 7, $M_n$ of the PPMs increased in a nearly linear fashion as the polymerization time increased from 3 h to 48 h, supporting a chain-growth mechanism. The small deviation in Mn and Ð m over multiple reactions demonstrates the reproducibility of this reaction. The molecular mass distribution of all polymerizations was around 1.6 without fractionation further demonstrating that the chain growth method affords more precise control over molecular mass distribution compared to a step-growth mechanism where Ð $_m$ is usually 2 or higher. Moreover, the yields for some of these reactions approach 65 percent, which is significantly greater than the yields for low molecular mass oligomers in known step growth processes.

In some embodiments, the molar ratio of either monomer to the initiator is from about 3:1 to 400:1. In some embodiments, the molar ratio of either monomer to the initiator is from about 3:1 to 300:1. In some embodiments, the molar ratio of either monomer to the initiator is from about 3:1 to 200:1. In some embodiments, the molar ratio of either monomer to the initiator is from about 3:1 to 100:1. In some embodiments, the molar ratio of either monomer to the initiator is from about 10:1 to 124:1.

The reaction shown in Step I of Scheme 1 above, takes place in one or more solvents B. In one or more embodiments, B may be any suitable solvent including, but not limited to, toluene, tetrahydrofuran (THF), dioxane, and combinations thereof. It is envisioned that whatever solvent is selected can be removed without undue difficulty or expense. In some embodiments, B is toluene. In some embodiments, the molar ratio of monomer to solvent is from about 5:1 to about 10:1. In some embodiments, the molar ratio of monomer to solvent is from about 6:1 to about 9:1. In some embodiments, the molar ratio of monomer to solvent is from about 7:1 to about 8:1. In some embodiments, the molar ratio of monomer to solvent is from about 5:1 to about 8:1 In some embodiments, the molar ratio of monomer to solvent is about 7.14:1.

In some embodiments of the present invention, the monomers and selected solvent B are placed in a suitable container, such as a round bottom flask, and the monomers dissolved at ambient temperature using a magnetic stirrer. It should be understood, however, any method known in the art may be used to dissolve the monomers in the solvent, provided that it does not inactivate the initiator. In addition, it will be appreciated by those of skill in the art that the monomers should be dissolved and reacted in an inert gas atmosphere. One of ordinary skill in the art will be able to select an inert gas for the inert atmosphere without undue experimentation. Suitable inert gasses include, without limitation, nitrogen, argon, or helium. In some embodiments, the system is cooled to ambient temperature under a nitrogen or argon atmosphere.

In these embodiments, the container may be connected to a condenser and the mixture is then heated to a reaction temperature C. In some embodiments, the condenser may be a water reflux condenser or other conventional cooling system. The method used to bring the temperature of the mixture to the reaction temperature is not particularly limited and may include, without limitation, a silicone oil bath, water bath, or electric jacket. It should be apparent that the reaction temperature C plays an important role in the nature and kinetics of the reaction of Step I and is generally in the range of from about 60° C. to about 120° C., but can also be done at room temperature in some embodiments. (See Tables 3 and 6, below). It should be appreciated, however, that at lower temperatures (below about 50° C.) may have random polymerization. In some embodiments, C may be from about 60° C. to about 120° C. In some embodiments, C may be from about 70° C. to about 100° C. In some embodiments, C may be from about 70° C. to about 90° C. In some embodiments, C may be from about 75° C. to about 80° C. In some embodiments, C is about 80° C.

TABLE 3

|  | T (° C.) | | |
| --- | --- | --- | --- |
|  | 80 | 90 | 100 |
| $M_n$ (Da) | 550 | 650 | 770 |
| $M_p$ (Da) | 650 | 900 | 910 |
| $Ð_m$ | 1.2 | 1.5 | 1.5 |

Further, as can be seen in Table 2 above and Table 4, below, the reaction time D also plays an important role in the nature and kinetics of the reaction of Step I. In general, the longer the reaction time, the larger the $M_n$ for the PPM produced. As will be apparent to those of skill in the art, at very short reaction times (less than 0.5 h) the reaction is highly inefficient as there is little polymer produced and large quantities of unreacted monomer that must be removed. At reaction times over 100 hours, the polymer may become so viscous that it cannot be stirred using a magnetic stirrer and polymerization becomes more difficult to control. In some embodiments, D may be from 0.5 hours to 100 hours. In some embodiments, D may be from 3 hours to 75 hours. In some embodiments, D may be from 3 hours to 50 hours. In some embodiments, D may be from 12 hours to 50 hours. In some embodiments, D may be from 40 hours to 60 hours. In some embodiments, D is 40 hours.

TABLE 4

| | | | | Synthesis Conditions | | | | |
| --- | --- | --- | --- | --- | --- | --- | --- | --- |
| Name | Time (h) | $M_n$ (Da) | $Ð_m$ | MAn/Toluene (mol/L) | Molar ratio of MAn/PO in feed | Molar ratio of MAn to Mg(OEt)$_2$ | Temp (° C.) | Mole of MAn (mmol) |
| PPM 20140919 | 20 | 1060 | 1.76 | 7.14 | 1 | 200 | 80 | 714 |
|  | 50 | 2900 | 1.53 | | | | | |
|  | 70 | 3600 | 1.48 | | | | | |
|  | 90 | 3240 | 1.58 | | | | | |
|  | 114 | 3310 | 1.64 | | | | | |
|  | 138 | 3740 | 1.57 | | | | | |

In some embodiments, A is magnesium ethoxide (Mg(OEt)$_2$), B is toluene, C is 80° C., D is 2 hours and the PPM produced had a $M_n$ of 1700 Daltons, a Ð $_m$ of 1.64 and a yield of 58.97%. In some embodiments, A is magnesium ethoxide (Mg(OEt)$_2$), B is toluene, C is 80° C., D is 40 hours and the PPM produced had an $M_n$ of 1192 Daltons and a $Đ_m$ of 1.42. In some embodiments, A is magnesium ethoxide (Mg(OEt)$_2$), B is toluene, C is 80° C., D is 2 hours and the PPM produced had an $M_n$ of 1206 Daltons and a $Đ_m$ of 1. In some embodiments, A is magnesium ethoxide (Mg(OEt)$_2$), B is toluene, C is 80° C., and D, $M_n$, $M_P$, and $Đ_m$ of the PPM polymers produced are all as set forth in Table 2. In some embodiments, A is magnesium ethoxide (Mg(OEt)$_2$), B is toluene, C is 80° C., and D, $M_n$, and $Đ_m$ of the PPM polymers produced are all as set forth in Table 4.

When the reaction is complete, the PPM intermediate may be isolated and purified by any suitable methods known in the art for that purpose. Suitable methods may include, without limitation, extraction and concentration. In some embodiments, once the designated polymerization time has passed, the system is cooled to a temperature of from about 80° C. to about 20° C. under an inert atmosphere. The method for cooling the system is not particularly limited and may include, without limitation ice bath, recirculating bath, or ambient air temperature. Similarly, one of ordinary skill in the art will be able to select an inert gas for the inert atmosphere without undue experimentation. Suitable inert gasses include, without limitation, nitrogen, argon, or helium. In some embodiments, the system is cooled to ambient temperature under a nitrogen or argon atmosphere.

Next in these embodiments, the volatile compounds are removed by evaporation using any method known in the art for that purpose. In some embodiments, the volatile compounds may be removed by distillation, rotary evaporation or evaporation under reduced pressure. In some of these embodiments, the resulting polymer is then diluted with an organic solvent such as chloroform (CHCl$_3$) or dichloromethane CH$_2$Cl$_2$. In some embodiments, the polymer may be diluted with chloroform.

The polymer solution in these embodiments is then washed with water or an aqueous solution. In some embodiments, the polymer solution is washed with water containing an oxidizer or acidic proton solution to remove the inorganic compounds. In some embodiments, the polymer solution is washed with water containing a trace amount of HCl. As should be appreciated, in embodiments where the polymer solution is washed in water or an aqueous solution, the polymer solution will separate to form an organic layer containing the polymer and an aqueous layer containing water soluble impurities. In these embodiments, the organic layer containing the polymer may then be collected by any conventional means, including but not limited to a separatory funnel. It should be noted that in some embodiments, the steps of diluting the polymer with an organic solvent like chloroform or dichloromethane and washing it with water or an aqueous solution may be repeated. In some embodiments, the PPM polymer may be washed with water from 1 to 10 times.

In some of these embodiments, after the desired number of washing steps have been done, the resulting organic layer containing the PPM polymer is then poured into an excess quantity of a non-polar organic solvent such as hexane, heptane, pentane, toluene, diethyl ether, or octane to precipitate the PPM polymer out of solution. It should be appreciated that in embodiments where it has a $M_n$ of less than about 4000 Daltons, the PPM polymer will be a viscous fluid and will separate from the non-polar organic solvent again forming two layers. The fluid polymer layer may then be collected by any conventional means, including but not limited to a separatory funnel. In embodiments, where the polymer is a solid, it may be removed from the organic solvent by any conventional means for isolation and collecting solids, including but not limited to filtration or centrifugation.

In these embodiments, the resulting polymer may be again dissolved in a minimal amount of an organic solvent, such as chloroform of dichloromethane and then concentrated by distillation or rotary evaporation. Finally, in these embodiments, the purified PPM intermediate may then be obtained by drying the product under a vacuum overnight at room temperature to remove all volatiles.

In some embodiments, the reaction of Step I in Scheme 1 may comprise dissolving molar equivalents of maleic anhydride and propylene oxide in a suitable solvent, such as toluene, at ambient temperature under nitrogen. After all monomers are dissolved in toluene with magnetic stirring, Mg(OEt)$_2$ is added to the mixture in a ratio of 1 mole of Mg(OEt)$_2$ for every 24 moles of monomers and the flask is moved into a silicone oil bath equipped with a water reflux condenser to start polymerization at 80° C. for 40 h. After the designated polymerization time of 40 hours has passed, the system is then cooled to room temperature under nitrogen and all volatiles removed by evaporation. In these embodiments, the resulting polymer is then diluted with CHCl$_3$, washed with water containing a trace amount of HCl to remove the inorganic compounds. The organic layer is then poured into hexane after rotary evaporation, and the precipitated polymer mixture is re-dissolved in a minimal amount of CHCl$_3$ and then concentrated by rotary evaporation. The PPM intermediate is then obtained after drying the product under vacuum overnight at room temperature to remove all volatiles.

Figure 2:
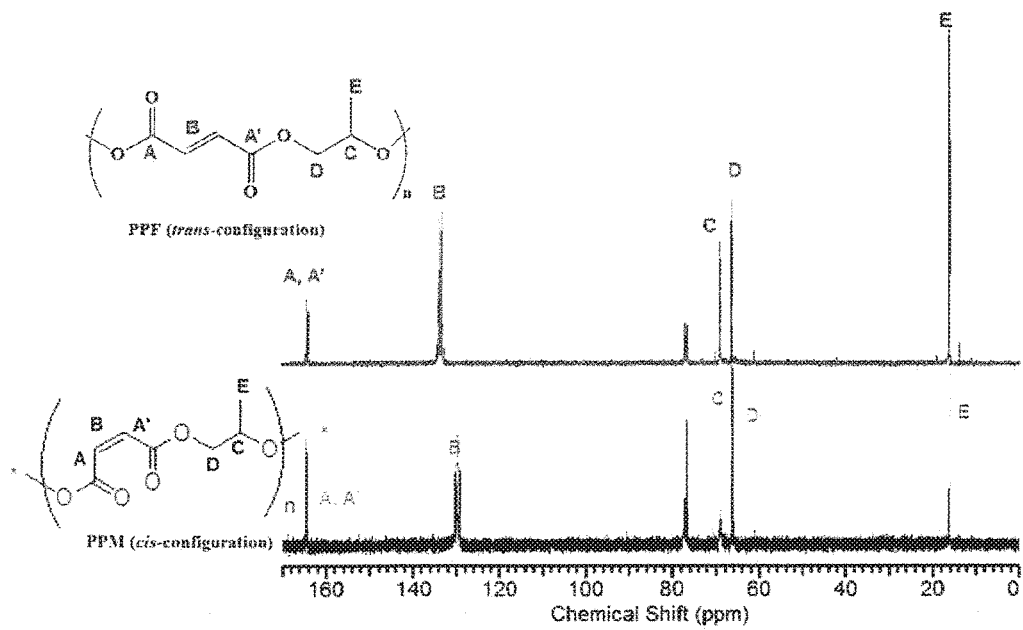
FIG. 2 is a schematic comparing $^{13}$C NMR spectra ($CDCl_3$, 300 MHz) for a PPM intermediate and PPF polymer according to one or more embodiments of the present invention indicating complete conversion of the PPM intermediate to the PPF polymer.

As set forth above, the second reaction (Step II) in Scheme 1 involves isomerization of the PPM synthesized in Step I into the trans-isomer to form PPF. It has been found that even a relatively small amount of PPM polymer chains remain in the PPF polymer, it will adversely affect the ability of the polymer to cross link, rendering it unsuitable for 3D printing and other similar applications. Accordingly, it is important that essentially all of the PPM be converted to PPF. FIG. 1 is a schematic comparing $^1$H NMR spectra (CDCl$_3$, 300 MHz) for the PPM intermediate and PPF polymer according to one or more embodiments of the present invention indicating that confirming that no measurable PPM remains in the polymer. The residual solvent used in the purification step can be further removed with longer times under vacuum. The spectra in FIG. 1 shows that PPM was successfully isomerized to PPF with the location of the resonances of the cis-alkene protons ($\delta$=6.2) on C=C bonds shifting to the expected position for protons in the trans-configuration ($\delta$=6.8).

Figure 8:
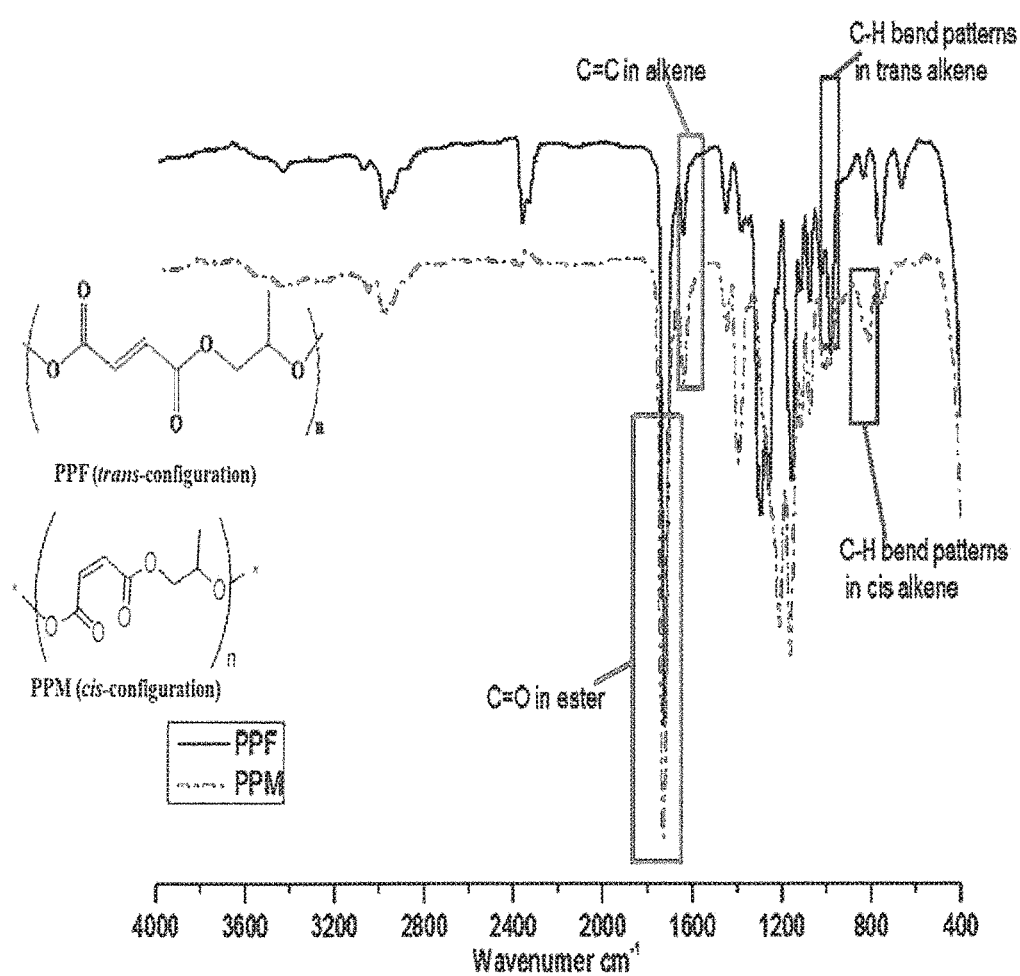
FIG. 8 a schematic comparing Fourier Transform Infrared. Spectroscopy (FTIR) spectra (film, KBr, $CHCl_3$, 400 $cm^{-1}$-4000 $cm^{-1}$) for a PPM intermediate and PPF polymer according to one or more embodiments of the present invention indicating complete conversion of the PPM intermediate to the PPF polymer. The cis to trans conversion is seen in C—H stretches.
Figure 9:
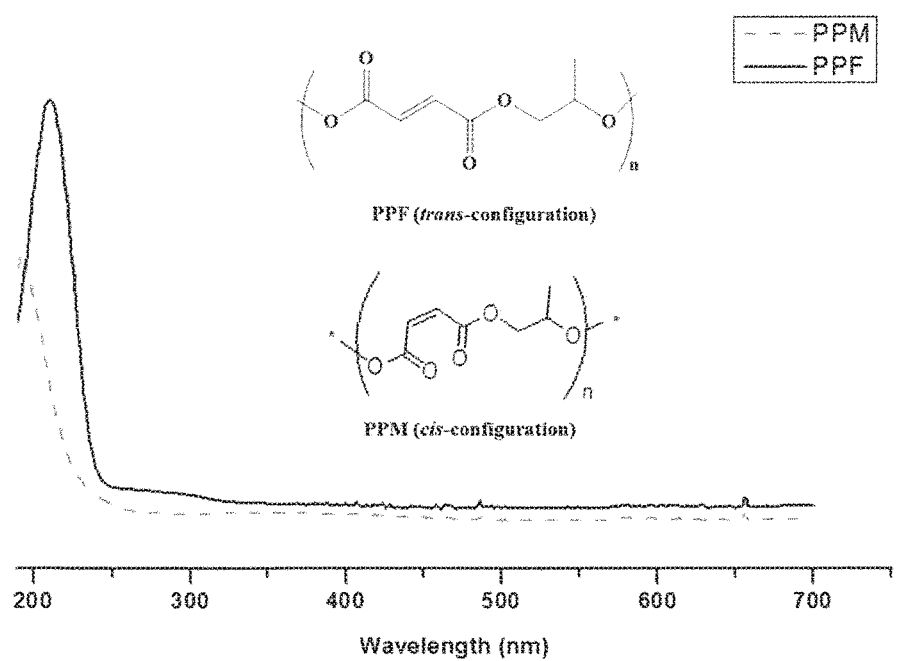
FIG. 9 a schematic comparing Ultraviolet-Visible Spectroscopy (UV-Vis) spectra (acetonitrile, 190 nm-700 nm) for a PPM intermediate and PPF polymer according to one or more embodiments of the present invention indicating complete conversion of the PPM intermediate to the PPF polymer.

FTIR and UV-vis spectrophotometry were used to further support the chemical structures of PPM and PPF. FIG. 8 a schematic comparing Fourier Transform Infrared Spectroscopy (FTIR) spectra (film, KBr, CHCl$_3$, 400 cm$^{-1}$-4000 cm$^{-1}$) for the PPM intermediate and PPF polymer according to one or more embodiments of the present invention confirming that no measurable PPM remains in the PPF polymer. In the PPM spectra in FIG. 8, the peak at 1715-1740 cm$^{-1}$ represented the unsaturated C=O (ester) stretch, which demonstrated the formation of the ester bond in the PPM synthesis process. Stretches at 2988 cm$^{-1}$, 1642 cm$^{-1}$, 1162 cm$^{-1}$, 814 cm$^{-1}$ showed C—H stretch, C=C (alkene) stretch, O—C (alkoxy) stretch, and C—H (cis alkene) bend (broad) patterns separately. In the spectra of PPF, the peak at 1715-1740 cm$^{-1}$ represented the unsaturated C=O (ester) stretch peak. Stretches at 2986 cm$^{-1}$, 1646 cm$^{-1}$, 1156 cm$^{-1}$, 984 cm$^{-1}$ were C—H stretch, C=C (alkene) stretch, O—C (alkoxy) stretch and C—H (trans alkene) bend patterns respectively. The appearance of C—H (trans alkene) bending stretches at 960-990 cm$^{-1}$ in the solid line curve demonstrated the isomerization process. These characteristic signals supported the successful synthesis of PPM and isomerization of PPM to PPF. See FIG. 8. Ultraviolet-visible spectroscopy clearly shows (acetonitrile, 190 nm-700 nm) for a PPM intermediate and PPF. In FIG. 9, the dashed line curve shows the UV-Visible spectra of PPM intermediate and the solid line curve shows the UV-Visible spectra of the PPF polymer. As can be seen, the dashed line curve has a strong absorbance at λ=192 nm, which corresponded to the π-π* transition of cis-configuration C═C bonds in PPM. In the solid line spectrum of PPF, there is a strong absorbance at λ=210 nm, which was the π-π* transition of trans-configuration C═C bond in PPF. The shift results from the conversion of a higher energy cis-configuration C═C bonds to a lower energy trans configuration.

In some embodiments, the conversion rate of PPM to PPF is from about 96 mass percent to about 100 mass percent. In some embodiments, the conversion rate of PPM to PPF is from about 98 mass percent to about 100 mass percent. In some embodiments, the conversion rate of PPM to PPF is from about 99 mass percent to about 100 mass percent. In some embodiments, the PPF polymer of the present invention contains no residual PPM polymer chains.

In the embodiments of the present invention shown in Step II of Scheme 1 above, the PPM intermediate placed in a suitable container, such as a round bottom flask, and dissolved in a suitable solvent F. In one or more embodiments, F may be any suitable solvent including, but not limited to, chloroform, tetrahydrofuran (THF), dioxane, diethyl ether, and combinations thereof. It is envisioned that whichever solvent is selected can be removed without undue difficulty or expense. In some embodiments, F may be chloroform.

In some embodiments, the Step II takes place under an inert atmosphere. Again, one of ordinary skill in the art will be able to select an inert gas for the inert atmosphere without undue experimentation. Suitable inert gasses include, without limitation, nitrogen, argon, or helium. In some embodiments, the system is cooled to ambient temperature under a nitrogen or argon atmosphere.

Once the PPM intermediate has been dissolved, a catalyst E is added. While other embodiments are possible, catalyst E is preferably diethylamine. In one or embodiments, the container is then connected to a condenser and the heated to a reaction temperature G. In some embodiments, the condenser may be a water reflux condenser or other conventional cooling system used in the art for this purpose. The method used to bring the temperature of the mixture to the reaction temperature G is not particularly limited and may include, without limitation, a silicone oil bath, a water bath, or an electric jacket.

In some embodiments, G may be a reaction temperature of from about 5° C. to about 80° C. In some embodiments, G may be a reaction temperature of from about 5° C. to about 80° C. In some embodiments, G may be a reaction temperature of from about 20° C. to about 70° C. In some embodiments, G may be a reaction temperature of from about 20° C. to about 60° C. In some embodiments, G may be a reaction temperature of from about 30° C. to about 60° C. In some embodiments, G may be a reaction temperature of from about 40° C. to about 60° C. In some embodiments, G may be a reaction temperature of from about 50° C. to about 60° C. In some embodiments, G may be a reaction temperature of about 20° C. In some embodiments, G may be a reaction temperature of about 55° C. In some embodiments, G may be a reaction temperature of about 58° C. In some embodiments, G may be a reaction temperature of about 60° C. In some embodiments, G may be a reaction temperature may be ambient temperature.

In some embodiments, H may be a reaction time of from about 5 to about 100 hours. In some embodiments, H may be a reaction time of from about 15 to about 50 hours. In some embodiments, H may be a reaction time of from about 20 to about 50 hours. In some embodiments, H may be a reaction time of about 20 hours. In some embodiments, H may be a reaction time of about 24 hours. In some embodiments, H may be a reaction time of about 40 hours. In some embodiments, H may be a reaction time of about 48 hours.

When the isomerization reaction is complete, the PPF polymer may be isolated and purified by any suitable methods known in the art for that purpose. In some embodiments, once the reaction time has lapsed, the reaction mixture containing the PPF polymer may first be concentrated by evaporation. In some of these embodiments, the reaction mixture may be concentrated by rotary evaporation or evaporation under reduced pressure. In these embodiments, the concentrated reaction mixture may then be washed with a buffered aqueous solution to remove the catalyst. While other embodiments are possible, it is envisioned that in these embodiments, the buffered aqueous solution will buffer to a neutral pH in the range of from about 6 to about 8. In some embodiments, the concentrated reaction mixture may be washed with a phosphate buffer saline solution. In some embodiments, the concentrated reaction mixture may be washed with a 0.5 molar phosphate buffer saline solution, configured to buffer to a pH of from about 6 to about 8.

In these embodiments, it should be understood that the reaction mixture will separate into an organic layer containing the PPF polymer and an aqueous layer containing water soluble impurities. The organic layer may then be collected by any conventional means, including but not limited to a separatory funnel. It should be noted that in some embodiments, the steps of washing the reaction mixture with a buffered aqueous solution may be repeated. In some embodiments, the reaction mixture may be washed with a buffered aqueous solution from 1 to 10 times. In some embodiments, the reaction mixture may be washed three times of BPS and then three times of saturated brine). Once these washing steps are complete, the solution is concentrated by evaporation. In some embodiments, the organic layer containing the polymer may be concentrated by rotary evaporation or deduced pressure. In these embodiments, an inorganic drying agent, acidic proton or molecular sieve, is then added to the concentrated polymer solution to remove any remaining water. In some embodiments, the inorganic drying agent, acidic proton or molecular sieve may comprise sodium sulfate. The solution is then filtered to remove the inorganic drying agent, acidic proton or molecular sieve.

Once the remaining water has been removed, the solution is added to an excess of a non-polar organic solvent, such as hexane, causing the PPF polymer to precipitate. It should be appreciated that in embodiments where it has a $M_n$ of less than about 4000 Daltons, the PPF polymer will be a viscous fluid and will separate from the non-polar organic solvent, again forming two layers. The fluid polymer layer may then be collected by any conventional means, including but not limited to a separatory funnel. In embodiments, where the polymer is a solid, it may be removed from the organic solvent by any conventional means for isolation and collecting solids, including but not limited to filtration or centrifugation.

The collected precipitate is then kept in a vacuum for from 12 to 24 hours to remove all remaining volatile compounds. In some embodiments, overnight at room temperature to remove all remaining volatile compounds.

In some embodiments, the reaction of Step II in Scheme 1 may comprise adding a catalyst, such as diethylamine (0.1 eq.), to the PPM intermediate, after dissolving the PPM polymer in $CHCl_3$ (1 mol/L) in a round-bottomed flask equipped with a water reflux condenser. Isomerization is conducted at about 55° C. for about 20 hours under a nitrogen atmosphere. The resulting mixture is then concentrated by rotary evaporation and washed with phosphate buffer saline solution (0.5M, pH=6) to remove the diethylamine. The organic layer is then collected after separation and sodium sulfate is added into the organic layer to remove water. The concentrated organic layer is then precipitated into hexane several times to remove impurities. The precipitate is collected and kept in vacuo overnight at room temperature to remove all volatiles, to leave a PPF polymer according to one or more embodiment of the present invention.

The low molecular weight, non-toxic, resorbable PPF polymers and the novel methods for making PPF polymers described above, represent a significant improvement over comparable polymers and methods known in the art. The PPF polymers described above have overcome the difficulties in controlling the molecular mass distribution inherent in the various step-growth polymerization methods known in the art. The low molecular weight, non-toxic, resorbable PPF polymers produced using the methods described above, have low polydispersity and properties that are consistent from batch to batch. It is believed that this consistency may be sufficient to meet the Good Manufacturing Practices (GMP) requirements implemented by the FDA, required for cytotoxicity testing, material property testing, small animal models, large animal models and pilot human trials and/or applicable ASTM and ISO standards as well as FDA guidelines.

As will be apparent to those of skill in the art, the viscosity and therefore the flowability of the fluid polymer resin used is an important variable in certain 3D printing methods. In general, the more viscous (i.e. less flowable) the polymer resin used, the longer it takes to print the 3D object via a photo cross linking method (e.g., 3D Systems (Rock Hill, S.C.) stereolithography or using a Texas Instruments (Dallas, Tex.) Digital Light Processing™ chip. In some embodiments, flowability of 3D printing resins prepare using polymers according to embodiments of the present invention may be increased by heating the resin or by the addition of non-toxic solvents, such as DEF. In practice, these methods of reducing viscosity are limited since too much heat can result in autocatalysis of the polymer and if too much DEF is used it can dramatically reduce the material properties of the resulting part. In addition, because the $M_n$ and $Đ_m$ are predictable and well known, batches with different $M_n$ can be blended to get desired viscosity, degradation and/or other characteristics. It is believed that it may be possible use a low molecular weight PPF like a solvent to reduce the viscosity of the blended polymer, and with it the flowability of 3D printing resins made with PPF polymers of the present invention.

Further, the novel methods described above are scalable and constitute an unexpected and game-changing improvement in the time and expense necessary to synthesize PPF polymers, as compared with prior art for step-growth polymerization of PPF. In particular, known step-growth methods of synthesizing PPF polymers are slow, labor intensive and very expensive. Using these methods, it takes about two weeks to produce a variable amount of PPF polymer. This process requires nearly constant monitoring. It requires high energy (heat) input, high vacuum, long reaction times, and result in low conversion with uncontrolled molecular mass distribution, conjugate-addition side reactions, and unwanted cross-linking, all of which greatly influence the mechanical properties and degradation rates of the final product. What took weeks using prior art the step-growth polymerization methods, can be accomplished in 3 to 7 days depending on quantity with standard (inexpensive) equipment, using methods according to embodiments of the present invention, as set forth herein. Using standard laboratory equipment the cost per gram is dramatically reduced. Moreover, the scalability of these methods greatly compounds the savings of time and expense. It is believed that the novel methods described herein greatly reduce the cost per kilogram, using GMP-level procedures and equipment. Indeed, it is believed that these methods may make the activity commercially feasible.

In addition, the present invention overcomes problems inherent in using known PPF polymers prepared using ring-opening methods for 3D printing. PPF polymers according to embodiments of the present invention that have relatively low molecular weights and while viscous, are flowable.

EXAMPLES

The following examples are offered to more fully illustrate the invention, but are not to be construed as limiting the scope thereof. Further, while some of examples may include conclusions about the way the invention may function, the inventors do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials and Methods

Unless otherwise set forth herein, the materials used are those set forth in Table 5.1, below.

TABLE 5.1

Materials/Reagents Used

| Name | Formula | Purity | Source |
|---|---|---|---|
| Maleic Anhydride (MAn) | $C_4H_2O_3$ | 99% | Fluka |
| Propylene Oxide (PO) | $C_3H_6O$ | 99.5% | Aldrich |
| Magnesium Ethoxide | $Mg(OEt)_2$ | 98% | Aldrich |
| Diethylamine | $C_4H_{10}N$ | 99%, extra pure | Sigma-Aldrich |
| Hydrochloric acid | HCl | ACS, 37% | Sigma-Aldrich |
| Toluene (Tol) | $C_7H_8$ | anhydrous, 99.8% | Sigma-Aldrich |
| Tetrahydrofuran (THF) | $C_4H_8O$ | ACS grade | Sigma-Aldrich |
| Chloroform | $CHCl_3$ | ACS grade | Sigma-Aldrich |

TABLE 5.1-continued

Materials/Reagents Used

| Name | Formula | Purity | Source |
| --- | --- | --- | --- |
| Hexane | $C_6H_{12}$ | 98.5% | Sigma-Aldrich |
| Sodium Phosphate Dibasic | $Na_2HPO_4$ | BioXtra, ≥99.0% | Sigma-Aldrich |
| Sodium Phosphate Monobasic | $NaH_2PO_4$ | BioXtra, ≥99.0% | Sigma-Aldrich |

Unless otherwise set forth herein, the analytical methods described herein were performed using the equipment and conditions set forth in Table 5.2, below.

TABLE 5.2

Analytical Methods/Equipment used

| Analytical Methods | Type/Equipment |
| --- | --- |
| $^1$H NMR | Varian Mercury 300 Spectrometer |
| $^{13}$C NMR | Varian Mercury 300 Spectrometer |
| Ubbelohde viscometer | Cannon State College, PA, 16804, 0016, USA, 50 L79 |
| UV Spectra | HP Hewlett Packard 8453 UV-Vis Instrument |
| FTIR (Fourier Transform Infrared Spectroscopy) | Excalibur Spectrometer Manual (FTS 3000 and FTS 4000 Series) |
| DSC (Differential Scanning Calorimetry) | TA instrument DSC Q2000 |
| SEC (Size Exclusion Chromatography) | GPCmax VE 2011 (with Waters 2414 Reflective Index Detector) |
| MALDI-TOF(Matrix-Assisted Laser Desorption/Ionization Time-of-Flight) | Bruker UltraFlex III MALDI tandem Time-of-Flight (TOF/TOF) mass spectrometer (Bruker Daltonics, Billerica, MA, USA) equipped with a Nd:YAG laser emitting at 355 nm |

$^1$H and $^{13}$C Nuclear magnetic resonance (NMR) spectra were recorded with a Varian NMRS 300 MHz instrument. Deuterated chloroform ($CDCl_3$) was used as solvent. Chemical shifts, δ (ppm), were referenced to the residual proton signal.

The chemical structures of PPF samples were further analyzed by a Bruker Ultraflex III Matrix-Assisted Laser Desorption/Ionization Time-of-Flight (MALDI-ToF/ToF) mass spectrometer. The samples were dissolved in $CHCl_3$ at a final concentration of 10 mg/mL. The sandwich method was used with trans-2-[3-(4-tert-Butylphenyl)-2-methyl-2-propenylidene] malononitrile (DCTB) as matrix and NaTFA as salt 10:1. End groups were identified for absolute molecular mass characterization.

FTIR spectra were recorded for film samples cast on potassium bromide (KBr) disks from $CHCl_3$ solution by an Excalibur Spectrometer (FTS 3000 and FTS 4000 Series) with a wavenumber range from 400 $cm^{-1}$ to 4000 $cm^{-1}$. The molecular mass and molecular mass distribution of each polymer was determined by size exclusion chromatography (SEC). SEC analysis in THF at 35° C. was performed on a Viscotek GPCmax VE 2011 GPC Solvent Sample Module with a Waters 2414 Reflective Index Detector, with polystyrene standards of narrow molecular mass distributions (with $M_W$ (g/mol): 580; 1280; 3180; 4910; 10440; 21,810; 51,150; 96,000; 230,900). The thermal properties of PPF were characterized by DSC using TA Q2000 differential scanning calorimeter from −100° C. to 100° C. at a scanning rate of 10° C./min in order to obtain the glass transition temperature ($T_g$).

Example 1.1

Representative Synthesis of Poly(maleic anhydride-co-propylene oxide)

Maleic anhydride (MAn) 70.06 g (714 mmol) and propylene oxide (PO) 50.0 mL (714 mmol) were dissolved in 100 mL of toluene in a 500 mL round-bottom flask at room temperature under a nitrogen atmosphere. After all of the monomers were dissolved in toluene with constant magnetic stirring, 272.34 mg (2.38 mmol, molar ratio of MAn/Mg $(OEt)_2$=300:1, $Mg(OEt)_2$ was added to the mixture and the flask was moved into a silicone oil bath equipped with a reflux condenser to initiate the polymerization at 80° C. The polymerization was allowed to proceed and aliquots were taken at defined time points (3 h, 6 h, 18 h, 24 h and 48 h). Similar studies incorporating molar ratio of MAn/Mg $(OEt)_2$=200:1, 100:1 were also conducted. After the designated polymerization time, the system was cooled to ambient temperature under nitrogen, and subjected to reduced pressure conditions to remove the volatile materials. The residue was diluted with chloroform ($CHCl_3$) washed with water containing trace amount of hydrochloric acid (HCl) to remove the inorganic $Mg(OEt)_2$ compound. The organic layer was poured into hexane following rotary evaporation, and the precipitated polymer mixture was re-dissolved in a minimal amount of $CHCl_3$. The residue was then concentrated by rotary evaporation. Poly(maleic anhydride-co-propylene oxide) was obtained after drying the product under vacuum overnight at ambient temperature to remove all volatiles, and then the molecular mass and mass distribution properties were characterized by Size Exclusion Chromatography (SEC) at each time point after $^1$H NMR characterization. $^1$H NMR (300 MHz, Chloroform-d δ ppm 1.13-1.41 (d, 3H, $OCH_2CH(CH_3)O$), 4.04-4.36 (m, 2H, $OCH_2CH(CH_3)O$), 5.23-5.30 (m, 1H, $OCH_2CH(CH_3)O$), 6.24-6.42 (m, 2H, CH═CH (cis-configuration)) See FIG. 1.

Example 1.2

General Procedure for the Isomerization of Poly(maleic anhydride-co-propylene oxide)

Diethylamine (0.15 eq.) was added to poly(maleic anhydride-co-propylene oxide) after dissolving the polymer in $CHCl_3$ in a round-bottom flask equipped with a water reflux condenser to start isomerization at 55° C. for 24 h under a nitrogen atmosphere. The mixture was then concentrated by rotary evaporation and washed with phosphate buffer saline solution (0.5M, pH=6) to remove the diethylamine. The organic layer was then precipitated into hexane several times to remove impurities. The precipitate was collected and kept in vacuo overnight at room temperature to remove all volatiles. Then, $^1$H NMR was used for characterization. $^1$H NMR (300 MHz, Chloroform-d) δ ppm 1.11-1.43 (d, 3H, $OCH_2CH(CH_3)O$), 4.09-4.39 (m, 2H, $OCH_2CH(CH_3)O$), 5.21-5.35 (m, 1H, $OCH_2CH(CH_3)O$), 6.83-6.91 (m, 2H, CH═CH (trans-configuration)).

Example 2

Large Batch Synthesis ($M_n$=1.5 kDa)

1. Synthesis of Poly(maleic anhydride-co-propylene oxide)

Maleic anhydride (2856 mmol) and propylene oxide (2856 mmol) were dissolved in toluene (400 mL) in a 2 L round-bottom flask at ambient temperature under nitrogen. After all monomers were dissolved in toluene with magnetic stirring, Mg(OEt)$_2$ (119 mmol; molar ratio of MAn:Mg (OEt)$_2$=24:1) was added to the mixture and the flask was moved into a silicone oil bath equipped with a water reflux condenser to start polymerization at 80° C. for 40 h. After the designated polymerization time, the system was cooled to room temperature under nitrogen, evaporated to remove all volatiles and then was diluted with CHCl$_3$, washed with water containing trace amount of HCl to remove the inorganic compound. The organic layer was poured into hexane after rotary evaporation, and the precipitated polymer mixture was re-dissolved in a minimal amount of CHCl$_3$ that was then concentrated by rotary evaporation. Poly(maleic anhydride-co-propylene oxide) (PPM) was obtained after drying the product under vacuum overnight at room temperature to remove all volatiles, and then the molecular mass and mass distribution properties were characterized by SEC after $^1$H-NMR characterization and $^{13}$C NMR characterization (SEC: M$_n$ 1200 Da; $^1$H NMR please see FIG. 1); $^{13}$C NMR shown in FIG. 2). $^{13}$C NMR (300 MHz, Chloroform-d) δ (ppm): 164.64, 164.63, 164.35; 130.42, 129.92, 129.78, 129.25; 69.15; 66.37; 16.19.

2. Isomerization of Poly(maleic anhydride-co-propylene oxide)

Diethylamine (0.15 equivalent) was added to poly(maleic anhydride-co-propylene oxide) after dissolving the polymer in CHCl$_3$ (1 mol/L) in a round-bottom flask equipped with a water reflux condenser to start isomerization at 55° C. for 20 h under nitrogen. The mixture was then concentrated by rotary evaporation and washed with phosphate buffer saline solution (0.5M, pH=6) to remove the diethylamine. The organic layer was collected after separation and sodium sulfate was added into the organic layer to remove water. The concentrated organic layer was then precipitated into hexane several times to remove impurities. The precipitate was collected and kept in vacuum overnight at room temperature to remove all volatiles, and then the molecular mass and mass distribution properties were characterized by SEC after $^1$H-NMR characterization. See Table 1 (PPF sample number 2, M$_n$ 1270 Da, Đ$_m$ 1.5) and FIG. 1.

Example 3

Large Batch Synthesis of PPF Polymers at 5 M$_n$ Levels (M$_n$=0.7 kDa, 1.27 kDa, 1.86 kDa, 2.45 kDa, and 3.16 kDa)

PPF polymers having M$_n$ of 0.7 kDa, 1.27 kDa, 1.86 kDa, 2.45 kDa, and 3.16 kDa were synthesized using the large batch PPF procedures described above in Example 2 using the polymerization parameters set forth in Table 6, below.

It should be noted that, that for PPF No. 1 the reaction auto-initiated at ambient temperature and reached a temperature of approximately 86° C. No heat was applied.

The positions and relative intensities of each characteristic peak or band in $^1$H NMR, $^{13}$C NMR, Matrix-Assisted Laser Desorption/Ionization Time-of-Flight, FTIR and UV-Vis spectra were used to prove the chemical structures of the products. Nuclear magnetic resonance (NMR) proton spectra and Nuclear magnetic resonance (NMR) carbon spectra were recorded with a Varian NMRS 300 MHz instrument. Deuterated chloroform (CDCl$_3$) was used as solvent. Chemical shifts, δ (ppm), were referenced to the residual proton signal. Chemical structures of PPF samples were further analyzed by a Bruker Ultraflex III MALDI-ToF/ToF mass spectrometer. The samples were dissolved in CHCl$_3$ at a final concentration of 10 mg/mL. The sandwich method was used with trans-2-[3-(4-tert-Butylphenyl)-2-methyl-2-propenylidene] malononitrile (DCTB) as matrix and NaTFA as salt 10:1. FTIR spectra were recorded for film samples cast on potassium bromide (KBr) disks from CHCl$_3$ solution by an Excalibur Spectrometer (FTS 3000 and FTS 4000 Series) with a wavenumber range from 400 cm$^{-1}$ to 4000 cm$^{-1}$. UV-visible spectra were obtained by dilute solutions of polymers in acetonitrile using a HP Hewlett Packard 8453 UV-Vis instrument with a wavelength range from 190 nm to 700 nm.

The molecular mass and molecular mass distribution of each polymer was determined by SEC. SEC analysis in THF at 35° C. was performed on a Viscotek GPCmax VE 2011 GPC Solvent Sample Module with a Waters 2414 Reflective Index Detector, with polystyrene standards of narrow molecular mass distributions (with M$_W$ (g/mol): 580, 1280, 3180, 4910, 10440, 21810, 51150, 96000, 230900).

The thermal properties of PPF were characterized by DSC using TA Q2000 differential scanning calorimeter from −100° C. to 100° C. at a scanning rate of 10° C./min in order to obtain the glass transition temperature (T$_g$). The intrinsic viscosity of PPF samples at five molecular mass level was tested in THF by Ubbelohde viscometer at 35° C., using the procedures set forth in Example 4, below. See Table 1, above. (See also, FIG. 3).

Example 4

General Procedures for Intrinsic Viscosity Measurements of PPF Polymers

Unless otherwise indicated, the intrinsic viscosity of PPF samples synthesized in Example 3 was measured in THF using an Ubbelohde viscometer at 35° C. Each PPF sample (M$_n$: 0.7 kDa, 1.27 kDa, 1.86 kDa, 2.45 kDa, and 3.16 kDa) was weighed and diluted in THF in a volumetric flask (10 mL). Freshly distilled THF was added into the volumetric

TABLE 6

| PPF # | MAn or PO (mmol) | Monomer/Toluene (mol/L) | Molar ratio of Monomer/Mg(OEt)$_2$ | t (h) | T (° C.) | Molar ratio of PPM/DEA | PPM/CHCl$_3$ (mol/L) | T (° C.) | t (h) |
|---|---|---|---|---|---|---|---|---|---|
| 1 | 6962 | 7.14 | 5.7 | ~6 | no heat, 29-86 | 6.67 | 1 | 50 | 16 |
| 2 | 2856 | 7.14 | 24 | 40 | 80 | 6.67 | 1 | 60 | 16 |
| 3 | 2856 | 7.14 | 48 | 40 | 80 | 10 | 1 | 60 | 24 |
| 4 | 2856 | 7.14 | 200 | 42 | 80 | 10 | 1 | 60 | 22 |
| 5 | 714 | 7.14 | 200 | 138 | 80 | 6.67 | 1 | 55 | 20 | flask to the 10 mL mark with a 0.45 um filter and sealed. The capillary viscometer was cleaned with pure THF. A thermostated water bath was heated to maintain the temperature at 35° C. The capillary viscometer was pre-equilibrated in the thermostated bath for at least 15 minutes to establish the thermal equilibrium. An injector was used to make the liquid fill up to more than ⅓ of the top ball of the capillary viscometer and then allowed the liquid to flow down. A stopwatch was used to record the time when the liquid passed over the first line on the capillary viscometer and stopped recording when the liquid passed the second line on the capillary viscometer. The time of this period was recorded. The flow time was recorded at least 5 times. The capillary viscometer was refilled by a filter with 5.0 mL of the solution prepared of PPF and THF. The capillary viscometer was put back into the thermostated bath. The flow time was measured and recorded for at least 3 times as described above. Then 5.0 mL, 3.0 mL and further 1.8 mL or 2.0 mL (results dependent) of pure THF solvent was added into the capillary viscometer using a filter respectively, and the corresponding flow time was measured and recorded for at least 3 times each. The calculations and experimental details for each PPF polymer are noted in Examples 5-9

Example 5

Intrinsic Viscosity of PPF Polymer ($M_n$=700 Da)

Experimental

Materials and Equipment. Thermostated bath, Ubbelohde capillary viscometer (Cannon State College, Pa., 16804, 0016, USA, 50 L79), stopwatch (accuracy: 0.01 s), poly(propylene fumarate) (PPF) samples, pure THF solvent, analytical balance, volumetric flasks (10 mL), filter (0.45 μm).

Preparation. Each PPF sample was weighed and diluted in THF in a volumetric flask (10 mL). Pure THF was added into the volumetric flask to the 10 mL line with a filter and then a stopper was plugged.

Measurement. The capillary viscometer was taken to be rinsed with pure THF firstly, which was then filled with pure THF to an appropriate level by a filter. The thermostated bath was heated to keep the temperature at 35° C. The capillary viscometer was kept in the thermostated bath for at least 15 minutes for establishing the thermal equilibrium. An injector was used to make the liquid fill up to more than ⅓ of the top ball of the capillary viscometer and then allowed the liquid to flow down. A stopwatch was used to record the time when the liquid flew over the first line on the capillary viscometer and stopped recording when the liquid passed the second line on the capillary viscometer. The time of this period was recorded. The flow time was measured for at least 5 times to get 3 times Δt among which no more than 0.2 s. Then the THF in the capillary viscometer was poured out. The capillary viscometer was refilled by a filter with 5 mL of the solution prepared of PPF and THF. The capillary viscometer was put back into the thermostated bath. The flow time was measured and recorded for at least 3 times as the procedures above. Then 5 mL, 3 mL and further 1.8 mL (results dependent) of pure THF solvent was added into the capillary viscometer by a filter respectively, and the corresponding flow time was measured and recorded for at least 3 times each as the procedures above.

Results and Discussion

Flow times. The flow times of the solutions with different concentrations ($c_0$, $c_1$, $c_2$, $c_3$, and $c_4$) were obtained in the experiment. The average values of the flow times and the errors were calculated. The representative data of 700 Da PPF are shown in Table 7.

TABLE 7

Flow times of 700 Da PPF solutions with different concentrations.

| 700 Da PPF | | THF | $c_1$ (5 mL) | $c_2$ (10 mL) | $c_3$ (13 mL) | $c_4$ (14.8 mL) |
|---|---|---|---|---|---|---|
| | c (g/L) | 0.00 | 410.00 | 205.00 | 157.69 | 138.51 |
| t(s) | $t_1$ | 123.56 | 693.03 | 264.97 | 219.28 | 201.88 |
| | $t_2$ | 123.66 | 692.90 | 264.82 | 219.28 | 201.84 |
| | $t_3$ | 123.46 | 695.22 | 264.92 | 219.25 | 201.79 |
| | $t_{ave}$ | 123.56 | 693.72 | 264.90 | 219.27 | 201.84 |
| | σ(s) | 0.10 | 1.30 | 0.08 | 0.02 | 0.05 |

Based on the data obtained from the experiment, a series of quantities were calculated by using the following equations.

$$\eta_r = \frac{\eta_i}{\eta_0} = \frac{t_i}{t_0} \quad (1)$$

$$\eta_{sp} = \eta_r - 1 \quad (2)$$

$$\eta_{inh} = \frac{\ln\eta_r}{c} \quad (3)$$

$$\eta_{red} = \frac{\eta_{sp}}{c} \quad (4)$$

wherein: $\eta_r$ is the relative viscosity, $\eta_{sp}$ is the specific viscosity, $\eta_{inh}$ is the inherent viscosity, $\eta_{red}$ is the reduced specific viscosity, $\eta_i$ is the viscosity of the solution and $\eta_0$ is the viscosity of the solvent; $t_i$ is the flow time of the solution and the $t_0$ is the flow time of the solvent; and c is the concentration of the solution. The results are shown in Table 8.

TABLE 8

The results of the calculations.

| solutions | $t_{ave}$ (s) | $\eta_r$ = t/$t_0$ | ln$\eta_r$ | (ln$\eta_r$)/c | $\eta_{sp}$ = ($\eta_r$ − 1) | $\eta_{sp}$/c |
|---|---|---|---|---|---|---|
| solvent | 123.56 | | | | | |
| $c_2$ | 264.90 | 2.143925 | 0.762638 | 0.003720 | 1.143925 | 0.005580 |
| $c_3$ | 219.27 | 1.774603 | 0.573577 | 0.003637 | 0.774603 | 0.004912 |
| $c_4$ | 201.84 | 1.633511 | 0.490732 | 0.003543 | 0.633511 | 0.004574 |

The intrinsic viscosity ([η]) may then be obtained by the Huggins equation and the Kraemer Equation where [η] is intrinsic viscosity and k', k" are constants.

The Huggins equation:

$$\eta_{sp}/c=[\eta]+k'[\eta]^2 c \quad (5)$$

The Kraemer Equation:

$$\ln(\eta_r)/c = [\eta] + k''[\eta]^2 c \quad (6)$$

Figure 10:
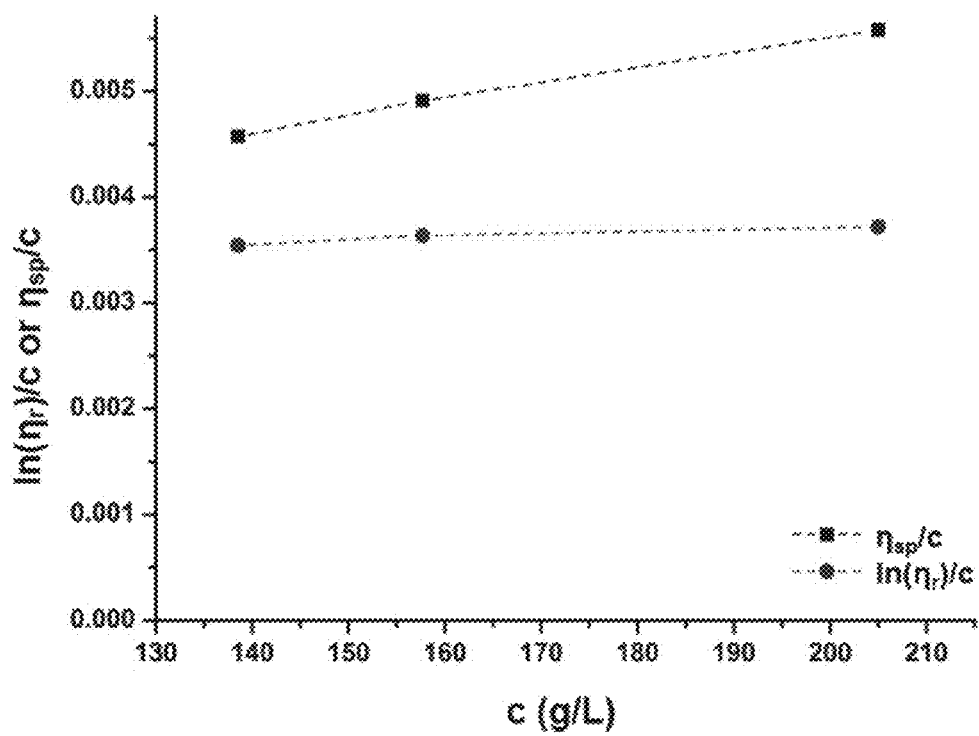
FIG. 10 is a graph showing $\eta_{sp}/c$ and $\ln(\eta_r)/c$ versus c for PPF sample number 1 in Table 1.

$\eta_{sp}/c$ and $\ln(\eta_r)/c$ were both plotted versus c as shown in FIG. 10 by origin 8.0. (See also Table 9, below). For the fitted line of $\eta_{sp}/c$ versus c on FIG. 10, the linear fit was obtained by origin 8.0.

TABLE 9

Linear fit values of 700 Da PPF solutions

|  |  | Value | Standard Error |
|---|---|---|---|
| $(\ln \eta_r)/c \sim c$ | Intercept | 0.00322 | 0.000120255 |
|  | Slope | 2.49391E-06 | 7.09936E-07 |
|  | Adj. R-Square | 0.85008 |  |
| $\eta_{sp}/c \sim c$ | Intercept | 0.00253 | 1.34E-04 |
|  | Slope | 1.49E-05 | 7.89E-07 |
|  | Adj. R-Square | 0.99444 |  |

According to FIG. 10, relationship between reduced viscosity and concentration is $\eta_{sp}/c = 0.00253 + 0.0000149\,c$. Compared with equation 5, we can get:

$[\eta] = 0.00253$ L/g $\sigma_{[\eta]} = 0.000134$ L/g $[\eta]_1 = (0.00253 \pm 0.000134)$ Similarly, the relationship between intrinsic viscosity and concentration is $\ln\eta_r/c = 0.00322 + 0.0000025c$, and by comparison with equation 6, obtained:

$[\eta]_2 = (0.00322 \pm 0.00012)$ L/g

The average of $[\eta]$ is treated as the final result:

$$[\eta]_{THF} = \frac{[\eta]_1 + [\eta]_2}{2} = \frac{0.00322 + 0.00253}{2} = 0.002875$$

$$\sigma_{[\eta]THF} = \frac{1}{2}\sqrt{0.00012^2 + 0.000134^2} = 0.0001$$

$[\eta] = 0.0029 \pm 0.0001$ L/g

Error analysis. The errors can come from many aspects. (1) The concentration of the solutions may not precise; (2) The flow time may not precise due to the error of eyes; (3) The temperature in the viscometer may not equal to the one of thermostated bath.

Example 6

Intrinsic Viscosity of PPF Polymer ($M_n = 1270$ Da)

Experimental

The Materials and Equipment and Preparation used in this Example were the same as those set forth in Example 4 and 5, above.

Measurement. The capillary viscometer was taken to be rinsed with pure THF firstly, which was then filled with pure THF to an appropriate level by a filter. The thermostated bath was heated to keep the temperature at 35° C. The capillary viscometer was kept in the thermostated bath for at least 15 minutes for establishing the thermal equilibrium. An injector was used to make the liquid fill up to more than 1/3 of the top ball of the capillary viscometer and then allowed the liquid to flow down. A stopwatch was used to record the time when the liquid flew over the first line on the capillary viscometer and stopped recording when the liquid passed the second line on the capillary viscometer. The time of this period was recorded. The flow time was measured for at least 5 times to get 3 times Δt among which no more than 0.2 s. Then the THF in the capillary viscometer was poured out. The capillary viscometer was refilled by a filter with 5 mL of the solution prepared of PPF and THF. The capillary viscometer was put back into the thermostated bath. The flow time was measured and recorded for at least 3 times as the procedures above. Then 5 mL, 3 mL and further 2 mL (results dependent) of pure THF solvent was added into the capillary viscometer by a filter respectively, and the corresponding flow time was measured and recorded for at least 3 times each as the procedures above.

Results and Discussion

Flow times. The flow times of the solutions with different concentrations ($c_0$, $c_1$, $c_2$, $c_3$, and $c_4$) were obtained in the experiment. The average values of the flow times and the errors were calculated. The representative data of 1270 Da PPF are shown in Table 10.

TABLE 10

Flow times of 1270 Da PPF solutions with different concentrations.

| 1270 Da PPF | | THF | $c_1$ | $c_2$ | $c_3$ | $c_4$ |
|---|---|---|---|---|---|---|
| c (g/L) | | 0.00 | 117.4 | 58.7 | 45.15 | 39.13 |
| t(s) | $t_1$ | 123.56 | 224.75 | 165.41 | 155.07 | 150.37 |
|  | $t_2$ | 123.66 | 224.56 | 165.48 | 154.94 | 150.28 |
|  | $t_3$ | 123.46 | 224.63 | 165.5 | 155.06 | 150.43 |
|  | $t_{ave}$ | 123.56 | 224.65 | 165.46 | 155.02 | 150.36 |
|  | $\sigma(s)$ | 0.1 | 0.10 | 0.05 | 0.07 | 0.07 |

Based on the data obtained from the experiment, a series of quantities were calculated by using the following equations.

$$\eta_r = \frac{\eta_i}{\eta_0} = \frac{t_i}{t_0} \quad (1)$$

$$\eta_{sp} = \eta_r - 1 \quad (2)$$

$$\eta_{inh} = \frac{\ln\eta_r}{c} \quad (3)$$

$$\eta_{red} = \frac{\eta_{sp}}{c} \quad (4)$$

wherein: $\eta_r$ is the relative viscosity, $\eta_{sp}$ is the specific viscosity, $\eta_{inh}$ is the inherent viscosity, $\eta_{red}$ is the reduced specific viscosity, $\eta_i$ is the viscosity of the solution and $\eta_0$ is the viscosity of the solvent; $t_i$ is the flow time of the solution and the $t_0$ is the flow time of the solvent; and c is the concentration of the solution. The results are shown in Table 11.

TABLE 11

The results of the calculations.

| solutions | $t_{ave}$ (s) | $\eta_r = t/t_0$ | $\ln\eta_r$ | $(\ln\eta_r)/c$ | $\eta_{sp} = (\eta_r - 1)$ | $\eta_{sp}/c$ |
|---|---|---|---|---|---|---|
| solvent | 123.56 | NA | NA | NA | NA | NA |
| $c_1$ | 224.65 | 1.818118 | 0.597802 | 0.005092 | 0.818118 | 0.006969 |
| $c_3$ | 155.02 | 1.254640 | 0.226849 | 0.005024 | 0.254640 | 0.005639 |
| $c_4$ | 150.36 | 1.216899 | 0.196306 | 0.005016 | 0.216899 | 0.005543 |

The intrinsic viscosity ($[\eta]$) may then be obtained by the Huggins equation and the Kraemer Equation where $[\eta]$ is intrinsic viscosity and k', k" are constants.

The Huggins equation:

$$\eta_{sp}/c = [\eta] + k'[\eta]^2 c \quad (5)$$

The Kraemer Equation:

$$\ln(\eta_r)/c = [\eta] + k''[\eta]^2 c \quad (6)$$

Figure 11:
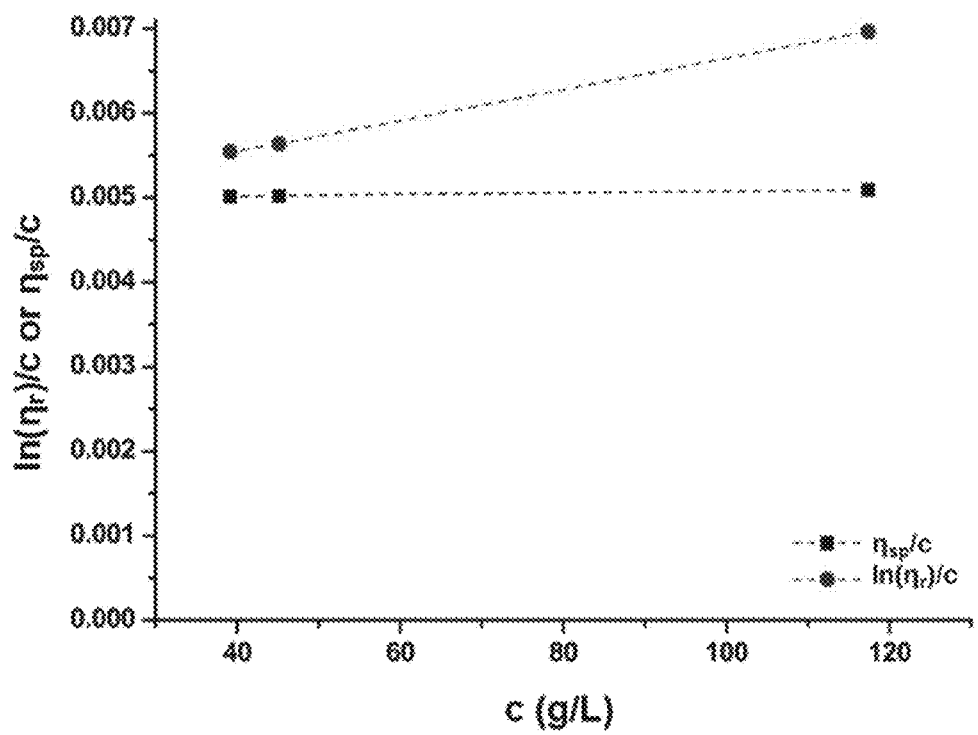
FIG. 11 is a graph showing $\eta_{sp}/c$ and $\ln(\eta_r)/c$ versus c for PPF sample number 2 in Table 1.

$\eta_{sp}/c$ and $\ln(\eta_r)/c$ were both plotted versus c as shown in FIG. 11 by origin 8.0. (See also Table 12, below). For the fitted line of $\eta_{sp}/c$ versus c on FIG. 11, the linear fit was obtained by origin 8.0.

TABLE 12

Linear fit values of 1270 Da PPF solutions

| | | Value | Standard Error |
|---|---|---|---|
| $(\ln \eta_r)/c \sim c$ | Intercept | 0.00322 | 0.000120255 |
| | Slope | 2.49391E−06 | 7.09936E−07 |
| | Adj. R-Square | 0.85008 | |
| $\eta_{sp}/c \sim c$ | Intercept | 0.00253 | 1.34E−04 |
| | Slope | 1.49E−05 | 7.89E−07 |
| | Adj. R-Square | 0.99444 | |

According to FIG. 11, relationship between reduced viscosity and concentration is $\eta_{sp}/c = 0.00498 + 0.000000957c$. Compared with equation 5, we can get:

$$[\eta] = 0.00498 \text{ L/g}$$

$$\sigma_{[\eta]} = 0.00000159 \text{ L/g}$$

$$[\eta]_1 = (0.00498 \pm 0.00000159)$$

Similarly, the relationship between intrinsic viscosity and concentration is $\ln\eta_r/c = 0.00482 + 0.0000183c$, and by comparison with equation 6, obtained:

$$[\eta]_2 = (0.00482 \pm 0.0000117) \text{ L/g}$$

The average of $[\eta]$ is treated as the final result:

$$[\eta]_{THF} = \frac{[\eta]_1 + [\eta]_2}{2} = \frac{0.00498 + 0.00482}{2} = 0.00490$$

$$\sigma_{[\eta]THF} = \frac{1}{2}\sqrt{0.00000159^2 + 0.0000117^2} = 5.9 \times 10^{-6}$$

$$[\eta] = 0.00490 \pm 0.00001 \text{ L/g}$$

Example 7

Intrinsic Viscosity of PPF Polymer ($M_n$=1860 Da)

Experimental

The Materials and Equipment and Preparation used in this Example were the same as those set forth in Example 4, above.

Measurement. The capillary viscometer was taken to be rinsed with pure THF firstly, which was then filled with pure THF to an appropriate level by a filter. The thermostated bath was heated to keep the temperature at 35° C. The capillary viscometer was kept in the thermostated bath for at least 15 minutes for establishing the thermal equilibrium. An injector was used to make the liquid fill up to more than ⅓ of the top ball of the capillary viscometer and then allowed the liquid to flow down. A stopwatch was used to record the time when the liquid flew over the first line on the capillary viscometer and stopped recording when the liquid passed the second line on the capillary viscometer. The time of this period was recorded. The flow time was measured for at least 5 times to get 3 times Δt among which no more than 0.2 s. Then the THF in the capillary viscometer was poured out. The capillary viscometer was refilled by a filter with 5 mL of the solution prepared of PPF and THF. The capillary viscometer was put back into the thermostated bath. The flow time was measured and recorded for at least 3 times as the procedures above. Then 5 mL, 3 mL and further 2 mL (results dependent) of pure THF solvent was added into the capillary viscometer by a filter respectively, and the corresponding flow time was measured and recorded for at least 3 times each as the procedures above.

Results and Discussion

Flow times. The flow times of the solutions with different concentrations ($c_0$, $c_1$, $c_2$, $c_3$, and $c_4$) were obtained in the experiment. The average values of the flow times and the errors were calculated. The representative data of 1860 Da PPF are shown in Table 13.

TABLE 13

Flow times of 1860 Da PPF solutions with different concentrations.

| 1860 Da PPF | | THF | $c_1$ | $c_2$ | $c_3$ | $c_4$ |
|---|---|---|---|---|---|---|
| | c (g/L) | 0.00 | 123.60 | 61.80 | 47.54 | 41.20 |
| t(s) | $t_1$ | 123.56 | 288.66 | 182.10 | 164.82 | 159.47 |
| | $t_2$ | 123.66 | 288.46 | 182.09 | 164.81 | 159.40 |
| | $t_3$ | 123.46 | 288.50 | 181.94 | 164.78 | 159.44 |
| | $t_{ave}$ | 123.56 | 288.54 | 182.04 | 164.80 | 159.44 |
| | σ(s) | 0.10 | 0.11 | 0.09 | 0.02 | 0.04 |

Based on the data obtained from the experiment, a series of quantities were calculated by using the following equations.

$$\eta_r = \frac{\eta_i}{\eta_0} = \frac{t_i}{t_0} \quad (1)$$

$$\eta_{sp} = \eta_r - 1 \quad (2)$$

$$\eta_{inh} = \frac{\ln \eta_r}{c} \quad (3)$$

$$\eta_{red} = \frac{\eta_{sp}}{c} \quad (4)$$

wherein: $\eta_r$ is the relative viscosity, $\eta_{sp}$ is the specific viscosity, $\eta_{inh}$ is the inherent viscosity, $\eta_{red}$ is the reduced specific viscosity, $\eta_i$ is the viscosity of the solution and $\eta_0$ is the viscosity of the solvent; $t_i$ is the flow time of the solution and the $t_0$ is the flow time of the solvent; and c is the concentration of the solution. The results are shown in Table 14.

TABLE 14

The results of the calculations.

| solutions | $t_{ave}$ (s) | $\eta_r = t/t_0$ | $\ln \eta_r$ | $(\ln \eta_r)/c$ | $\eta_{sp} = (\eta_r - 1)$ | $\eta_{sp}/c$ |
|---|---|---|---|---|---|---|
| solvent | 123.56 | NA | NA | NA | NA | NA |
| $c_1$ | 288.54 | 2.335222 | 0.848107 | 0.006862 | 1.335222 | 0.010803 |
| $c_2$ | 182.04 | 1.473319 | 0.387518 | 0.006271 | 0.473319 | 0.007659 |
| $c_3$ | 164.80 | 1.333792 | 0.288026 | 0.006059 | 0.333792 | 0.007022 |
| $c_4$ | 159.44 | 1.290358 | 0.254920 | 0.006187 | 0.290358 | 0.007048 |

The intrinsic viscosity ([η]) may then be obtained by the Huggins equation and the Kraemer Equation where [η] is intrinsic viscosity and k', k" are constants.

The Huggins equation:

$$\eta_{sp}/c = [\eta] + k'[\eta]^2 c \quad (5)$$

The Kraemer Equation:

$$\ln(\eta_r)/c = [\eta] + k''[\eta]^2 c \quad (6)$$

Figure 12:
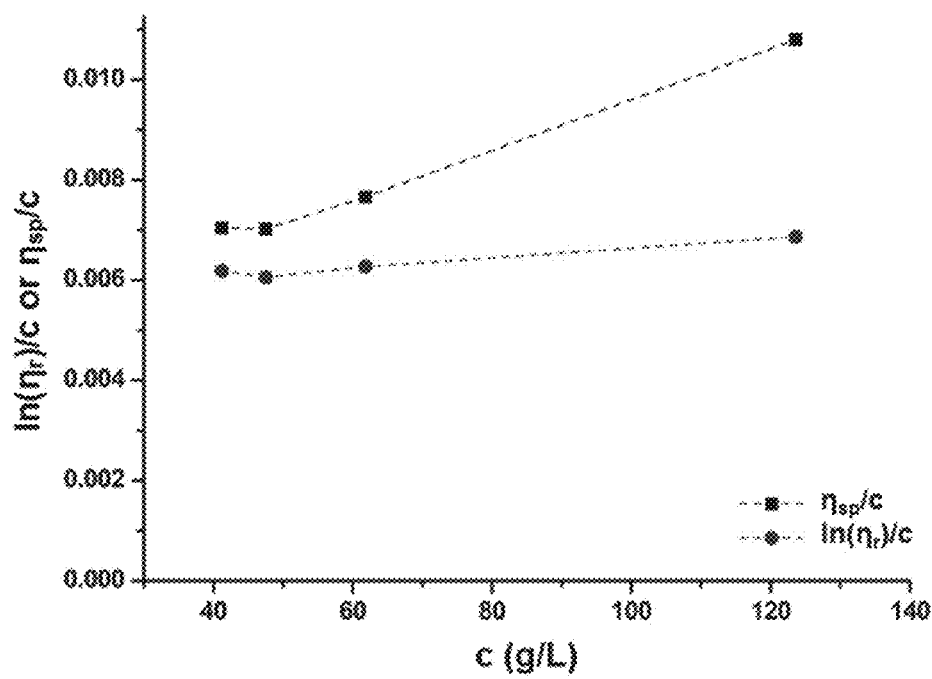
FIG. 12 is a graph showing $\eta_{sp}/c$ and $\ln(\eta_r)/c$ versus c for PPF sample number 3 in Table 1.

$\eta_{sp}/c$ and $\ln(\eta_r)/c$ were both plotted versus c as shown in FIG. 12 by origin 8.0. (See also Table 15, below). For the fitted line of $\eta_{sp}/c$ versus c on FIG. 12, the linear fit was obtained by origin 8.0.

TABLE 15

Linear fit values of 1860 Da PPF solutions

| | | Value | Standard Error |
|---|---|---|---|
| $(\ln \eta_r)/c \sim c$ | Intercept | 0.00571 | 1.09E−04 |
| | Slope | 9.21E−06 | 1.44E−06 |
| | Adj. R- | 0.92991 | |
| $\eta_{sp}/c \sim c$ | Intercept | 0.00487 | 2.40E−04 |
| | Slope | 4.76E−05 | 3.16E−06 |
| | Adj. R-Square | 0.98694 | |

According to FIG. 12, the relationship between reduced viscosity and concentration is $\eta_{sp}/c = 0.00487 + 0.0000476c$. Compared with equation 5, we can get:

[η]=0.00487 L/g [η]=0.00487 L/g $\sigma_{[\eta]}$=0.00024 L/g $\sigma_{[\eta]}$=0.00024 L/g

[η]$_1$=(0.00487±0.00024) L/g [η]$_1$= (0.00487±0.00024) L/g

Similarly, the relationship between intrinsic viscosity and concentration is $\ln \eta_r/c = 0.00571 + 0.00000921c$, and by comparison with equation 6, obtained:

[η]$_2$=(0.00571±0.000109) L/g [η]$_2$= (0.00571±0.000109) L/g

The average of [η] is treated as the final result:

$$[\eta]_{THF} = \frac{[\eta]_1 + [\eta]_2}{2} = \frac{0.00487 + 0.00571}{2} = 0.00529$$

$$\sigma_{[\eta]THF} = \frac{1}{2}\sqrt{0.00024^2 + 0.000109^2} = 0.00013$$

$$[\eta]_{THF} = \frac{[\eta]_1 + [\eta]_2}{2} = \frac{0.00487 + 0.00571}{2} = 0.00529$$

-continued $$\sigma_{[\eta]THF} = \frac{1}{2}\sqrt{0.00024^2 + 0.000109^2} = 0.00013$$

[η] = 0.00529 ± 0.00013 L/g

Example 8

Intrinsic Viscosity of PPF Polymer ($M_n$=2450 Da)

Experimental

The Materials and Equipment and Preparation used in this Example were the same as those set forth in Example 4, above.

Measurement. The capillary viscometer was taken to be rinsed with pure THF firstly, which was then filled with pure THF to an appropriate level by a filter. The thermostated bath was heated to keep the temperature at 35° C. The capillary viscometer was kept in the thermostated bath for at least 15 minutes for establishing the thermal equilibrium. An injector was used to make the liquid fill up to more than ⅓ of the top ball of the capillary viscometer and then allowed the liquid to flow down. A stopwatch was used to record the time when the liquid flew over the first line on the capillary viscometer and stopped recording when the liquid passed the second line on the capillary viscometer. The time of this period was recorded. The flow time was measured for at least 5 times to get 3 times Δt among which no more than 0.2 s. Then the THF in the capillary viscometer was poured out. The capillary viscometer was refilled by a filter with 5 mL of the solution prepared of PPF and THF. The capillary viscometer was put back into the thermostated bath. The flow time was measured and recorded for at least 3 times as the procedures above. Then 5 mL, 3 mL and further 2 mL (results dependent) of pure THF solvent was added into the capillary viscometer by a filter respectively, and the corresponding flow time was measured and recorded for at least 3 times each as the procedures above.

Results and Discussion

Flow times. The flow times of the solutions with different concentrations ($c_0$, $c_1$, $c_2$, $c_3$, $c_4$) were obtained in the experiment. The average values of the flow times and the errors were calculated. The representative data of 2450 Da PPF are shown in Table 16.

TABLE 16

Flow times of 2450 Da PPF solutions with different concentrations.

| | 2450 Da PPF | THF | $c_1$ | $c_2$ | $c_3$ | $c_4$ |
|---|---|---|---|---|---|---|
| | c (g/L) | 0.00 | 50.00 | 25.00 | 19.23 | 16.67 |
| t(s) | $t_1$ | 123.56 | 178.47 | 146.75 | 141.22 | 137.97 |
| | $t_2$ | 123.66 | 178.34 | 146.69 | 141.16 | 137.97 |
| | $t_3$ | 123.46 | 178.31 | 146.84 | 141.17 | 138.12 |
| | $t_{ave}$ | 123.56 | 178.37 | 146.76 | 141.18 | 138.02 |
| | σ(s) | 0.00 | 50.00 | 25.00 | 19.23 | 16.67 |

Based on the data obtained from the experiment, a series of quantities were calculated by using the following equations.

$$\eta_r = \frac{\eta_i}{\eta_0} = \frac{t_i}{t_0} \quad (1)$$

$$\eta_{sp} = \eta_r - 1 \quad (2)$$

$$\eta_{inh} = \frac{\ln\eta_r}{c} \quad (3)$$

$$\eta_{red} = \frac{\eta_{sp}}{c} \quad (4)$$

wherein: $\eta_r$ is the relative viscosity, $\eta_{sp}$ is the specific viscosity, $\eta_{inh}$ is the inherent viscosity, $\eta_{red}$ is the reduced specific viscosity, $\eta_i$ is the viscosity of the solution and $\eta_0$ is the viscosity of the solvent; $t_i$ is the flow time of the solution and the $t_0$ is the flow time of the solvent; and c is the concentration of the solution. The results are shown in Table 17.

TABLE 17

The results of the calculations.

| solutions | $t_{ave}$ (s) | $\eta_r = t/t_0$ | $\ln\eta_r$ | $(\ln\eta_r)/c$ | $\eta_{sp} = (\eta_r - 1)$ | $\eta_{sp}/c$ |
|---|---|---|---|---|---|---|
| solvent | 123.56 | NA | NA | NA | NA | NA |
| $c_1$ | 178.37 | 1.443617 | 0.367152 | 0.007343 | 0.443617 | 0.008872 |
| $c_2$ | 146.76 | 1.187763 | 0.172072 | 0.006883 | 0.187763 | 0.007511 |
| $c_4$ | 138.02 | 1.117028 | 0.110672 | 0.006640 | 0.117028 | 0.007022 |

The intrinsic viscosity ([η]) may then be obtained by the Huggins equation and the Kraemer Equation where [η] is intrinsic viscosity and k', k" are constants.

The Huggins equation:

$$\eta_{sp}/c = [\eta] + k'[\eta]^2 c \quad (5)$$

The Kraemer Equation:

$$\ln(\eta_r)/c = [\eta] + k''[\eta]^2 c \quad (6)$$

Figure 13:
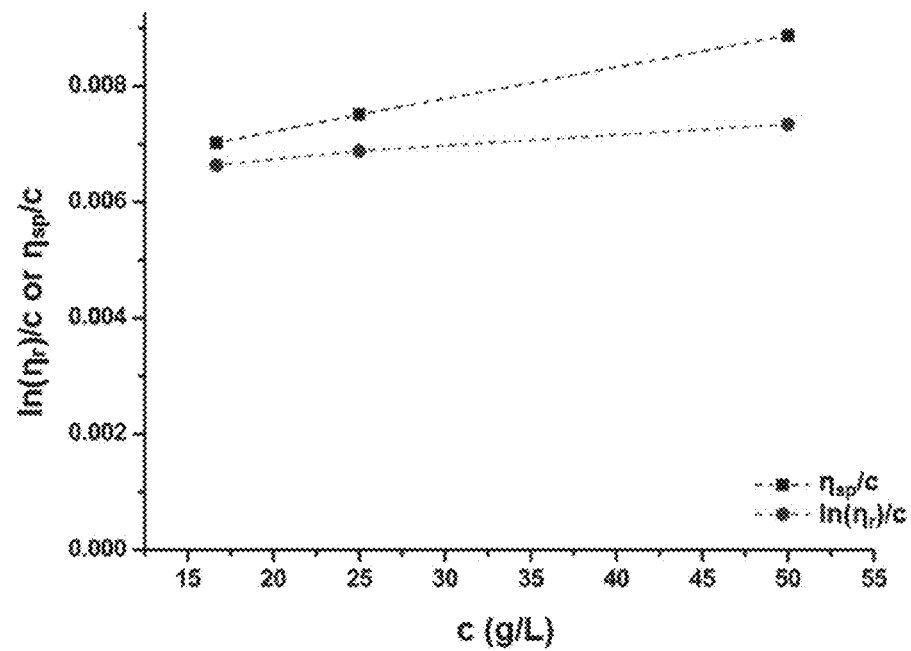
FIG. 13 is a graph showing $\eta_{sp}/c$ and $\ln(\eta_r)/c$ versus c for PPF sample number 4 in Table 1.

$\eta_{sp}/c$ and $\ln(\eta_r)/c$ were both plotted versus c as shown in FIG. 13 by origin 8.0. (See also Table 18, below). For the fitted line of $\eta_{sp}/c$ versus c on FIG. 13, the linear fit was obtained by origin 8.0.

TABLE 18

Linear fit values of 2450 Da PPF solutions

| | | Value | Standard Error |
|---|---|---|---|
| $(\ln\eta_r)/c\sim c$ | Intercept | 0.00633 | 7.20E−05 |
| | Slope | 2.05E−05 | 2.14E−06 |
| | Adj. R-Square | 0.97839 | |
| $\eta_{sp}/c\sim c$ | Intercept | 0.00611 | 2.82E−05 |
| | Slope | 5.53E−05 | 8.37E−07 |
| | Adj. R-Square | 0.99954 | |

According to FIG. 13, relationship between reduced viscosity and concentration is $\eta_{sp}/c=0.00611+0.0000553c$. Compared with equation 5, we can get:

[η]=0.00611 L/g $\sigma_{[\eta]}$=0.0000282 L/g

[η]$_1$=(0.00611±0.0000282) L/g

Similarly, the relationship between intrinsic viscosity and concentration is $\ln\eta_r/c=0.00633+0.0000205c$, and by comparison with equation 6, obtained:

[η]$_2$=(0.00633±0.000072) L/g

The average of [η] is treated as the final result:

$$[\eta]_{THF} = \frac{[\eta]_1 + [\eta]_2}{2} = \frac{0.00611 + 0.00633}{2} = 0.00622$$

$$\sigma_{[\eta]THF} = \frac{1}{2}\sqrt{0.0000282^2 + 0.000072^2} = 0.000055$$

[η] = 0.00622 ± 0.00006 L/g

Example 9

Intrinsic Viscosity of PPF Polymer ($M_n$=3160 Da)

Experimental

The Materials and Equipment and Preparation used in this Example were the same as those set forth in Example 4, above.

Measurement. The capillary viscometer was taken to be rinsed with pure THF firstly, which was then filled with pure THF to an appropriate level by a filter. The thermostated bath was heated to keep the temperature at 35° C. The capillary viscometer was kept in the thermostated bath for at least 15 minutes for establishing the thermal equilibrium. An injector was used to make the liquid fill up to more than ⅓ of the top ball of the capillary viscometer and then allowed the liquid to flow down. A stopwatch was used to record the time when the liquid flew over the first line on the capillary viscometer and stopped recording when the liquid passed the second line on the capillary viscometer. The time of this period was recorded. The flow time was measured for at least 5 times to get 3 times Δt among which no more than 0.2 s. Then the THF in the capillary viscometer was poured out. The capillary viscometer was refilled by a filter with 5 mL of the solution prepared of PPF and THF. The capillary viscometer was put back into the thermostated bath. The flow time was measured and recorded for at least 3 times as the procedures above. Then 5 mL, 3 mL and further 2 mL (results dependent) of pure THF solvent was added into the capillary viscometer by a filter respectively, and the corresponding flow time was measured and recorded for at least 3 times each as the procedures above.

Results and Discussion

Flow times. The flow times of the solutions with different concentrations ($c_0$, $c_1$, $c_2$, $c_3$, $c_4$) were obtained in the experiment. The average values of the flow times and the errors were calculated. The representative data of 3160 Da PPF are shown in Table 19.

TABLE 19

Flow times of 3160 Da PPF solutions with different concentrations.

| 3160 Da PPF | | THF | $c_1$ | $c_2$ | $c_3$ |
|---|---|---|---|---|---|
| | c (g/L) | 0.00 | 107.30 | 53.65 | 41.27 |
| t(s) | $t_1$ | 123.56 | 323.32 | 195.81 | 176.50 |
| | $t_2$ | 123.66 | 323.32 | 195.94 | 176.66 |
| | $t_3$ | 123.46 | 323.50 | 195.97 | 176.60 |
| | $t_{ave}$ | 123.56 | 323.38 | 195.91 | 176.59 |
| | σ(s) | 0.10 | 0.10 | 0.09 | 0.08 |

Based on the data obtained from the experiment, a series of quantities were calculated by using the following equations.

$$\eta_r = \frac{\eta_i}{\eta_0} = \frac{t_i}{t_0} \quad (1)$$

$$\eta_{sp} = \eta_r - 1 \quad (2)$$

$$\eta_{inh} = \frac{\ln \eta_r}{c} \quad (3)$$

$$\eta_{red} = \frac{\eta_{sp}}{c} \quad (4)$$

wherein: $\eta_r$ is the relative viscosity, $\eta_{sp}$ is the specific viscosity, $\eta_{inh}$ is the inherent viscosity, $\eta_{red}$ is the reduced specific viscosity, $\eta_i$ is the viscosity of the solution and $\eta_0$ is the viscosity of the solvent; $t_i$ is the flow time of the solution and the $t_0$ is the flow time of the solvent; and c is the concentration of the solution. The results are shown in Table 20.

TABLE 20

The results of the calculations.

| solutions | $t_{ave}$ (s) | $\eta_r = t/t_0$ | $\ln\eta_r$ | $(\ln\eta_r)/c$ | $\eta_{sp} = (\eta_r - 1)$ | $\eta_{sp}/c$ |
|---|---|---|---|---|---|---|
| solvent | 123.56 | NA | NA | NA | NA | NA |
| $c_1$ | 323.38 | 2.617190 | 0.962101 | 0.008966 | 1.617190 | 0.015072 |
| $c_2$ | 195.91 | 1.585519 | 0.460911 | 0.008591 | 0.585519 | 0.010914 |
| $c_3$ | 176.59 | 1.429157 | 0.357085 | 0.008653 | 0.429157 | 0.010399 |

The intrinsic viscosity ([η]) may then be obtained by the Huggins equation and the Kraemer Equation where [η] is intrinsic viscosity and k', k" are constants.

The Huggins equation:

$$\eta_{sp}/c = [\eta] + k'[\eta]^2 c \quad (5)$$

The Kraemer Equation:

$$\ln(\eta_r)/c = [\eta] + k''[\eta]^2 c \quad (6)$$

Figure 14:
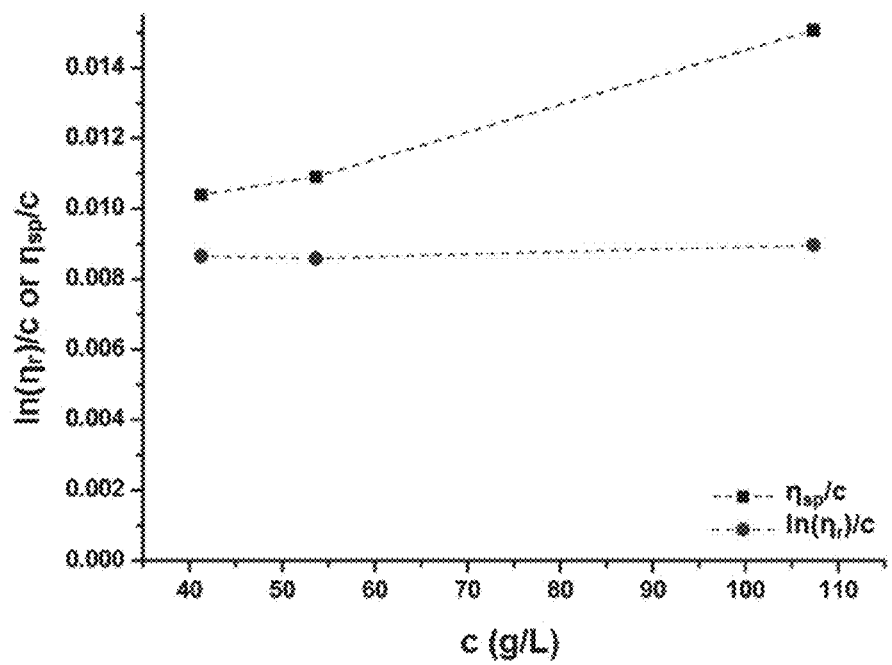
FIG. 14 is a graph showing $\eta_{sp}/c$ and $\ln(\eta_r)/c$ versus c for PPF sample number 5 in Table 1.

$\eta_{sp}/c$ and $\ln(\eta_r)/c$ were both plotted versus c as shown in FIG. 14 by origin 8.0. (See also Table 21, below). For the fitted line of $\eta_{sp}/c$ versus c on FIG. 14, the linear fit was obtained by origin 8.0.

TABLE 21

Linear fit values of 3160 Da PPF solutions

| | | Value | Standard Error |
|---|---|---|---|
| (lnηr)/c~c | Intercept | 0.00837 | 1.36E−04 |
| | Slope | 5.43E−06 | 1.86E−06 |
| | Adj. R-Square | 0.78926 | |
| ηsp/c~c | Intercept | 0.00722 | 4.10E−04 |
| | Slope | 7.28E−05 | 5.59E−06 |
| | Adj. R-Square | 0.98826 | |

According to FIG. 14, relationship between reduced viscosity and concentration is $\eta_{sp}/c = 0.00722 + 0.0000728c$. Compared with equation 5, we can get:

[η]=0.00722 L/g $\sigma_{[\eta]}$=0.00041 L/g

[η]$_1$=(0.00722±0.00041) L/g

Similarly, the relationship between intrinsic viscosity and concentration is $\ln\eta_r/c = 0.00837 + 0.00000543$ c, and by comparison with equation 6, obtained:

[η]$_2$=(0.00837±0.000136) L/g

The average of [η] is treated as the final result:

$$[\eta]_{THF} = \frac{[\eta]_1 + [\eta]_2}{2} = \frac{0.00722 + 0.00837}{2} = 0.007795$$

-continued $$\sigma_{[\eta]THF} = \frac{1}{2}\sqrt{0.00041^2 + 0.000136^2} = 0.00022$$

$$[\eta] = 0.00780 \pm 0.00022 \text{ L/g}$$

Example 10

Printing Resin Formulation

Poly (propylene fumarate) (PPF) with a molecular mass ($M_n$) of 1496 Da was used for the printing tests. Diethyl fumarate (DEF) (Sigma-Aldrich, St. Louis, Mo.) was added to the PPF in a 1:3 mass ratio in order to reduce the viscosity of the polymer. The DEF was used as a solvent, along with heat, to dissolve the photo initiators and oxybenzone prior to their addition to the resin at a mass ratio of 3:1 PPF to DEF. This mixture was stirred and heated at 200° F. in a fume hood. A resin suitable for photo cross linking was then created from the 3:1 PPF:DEF mixture by adding the photo initiators Irgacure 819 and Irgacure 784 (BASF, Ludwigshafen, Germany) as well as oxybenzone (Sigma-Aldrich), and additional DEF added to reach a mass ratio of 1:1 PPF:DEF. The final resin formulation had a mass ratio of 1:1 PPF to DEF and contained containing 3% Irgacure 819, 0.4% Irgacure 784, and 0.7% oxybenzone, by weight of PPF and DEF.

Example 11

Poly(propylene fumarate) Cure Tests

The EnvisionTEC Perfactory™ 3 Mini Multi Lens (Dearborn, Mich.) was used to perform cure tests on the PPF resin. Cure tests were conducted to measure the potential of the PPF to successfully print a 3D scaffold. Replicate tests (n=4) were conducted at exposure times of 30 seconds, 60 seconds, and 90 seconds. The exposure time relates to the time it would take to print one layer of a 3D scaffold. Prior to beginning the cure tests, the thicknesses of two microscope slides were measured using a material thickness gauge (MTG) (Checkline Electromatic, Cedarhurst, N.Y.). The Perfactory™ 3 was calibrated to generate a square UV mask with a targeted irradiance of 350 mW dm$^{-2}$. The thickness of one glass slide was taken into account during the calibration. The resin mentioned previously was heated and stirred in a fume hood at close to 200° F. to ensure homogeneity. To begin the cure tests, a pipette was used to place 5-7 drops of resin onto the center of the microscope slide that was used for calibration. The exposure time was adjusted on the Perfactory™ 3 to reflect the appropriate test time. The slide was placed onto the calibration plate in the Perfactory™ 3, above a square mask of UV light, and the cure test was initiated. Upon completion of the cure test, the slide was removed from the printer. The slide was flipped over so that the top of the slide containing the resin could be blotted. This was done to ensure that any excess liquid resin was removed from the slide and that only the cured square of resin remained. Another slide, the one that was measured prior to testing, was placed on top of the slide containing the cured material. This stack of slides was measured using the MTG. The thickness of the two slides with the cured material between them was compared to the thickness of the two slides stacked upon one another with no material between them. The difference was taken between these two measurements to obtain the thickness of the cured material. This process was repeated for each cure test (n=4).

Example 12

3D Photochemical Printing (350 µm Pore Size)

Figure 15:
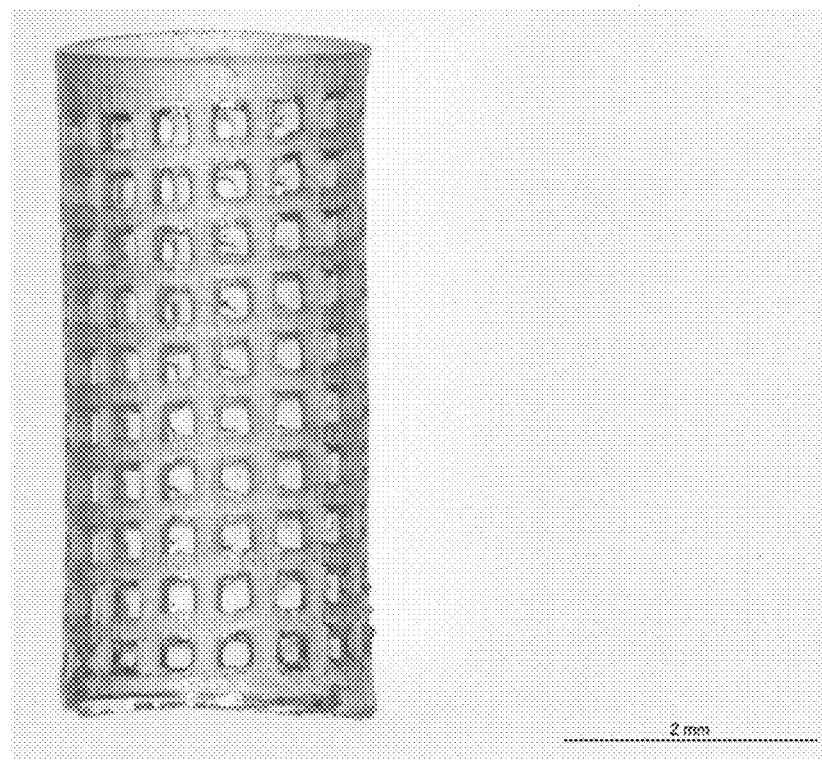
FIG. 15 is an image of a tissue scaffold made by a 3D printing process using a PPF polymer made according to the one or more embodiments of the present invention. Scale bar is 2 mm.

To begin printing the 3D scaffolds, an EnvisionTEC Perfactory™ 3 3D printer was calibrated to generate a UV mask with a nominal irradiance of 350 mW dm$^{-2}$. A scaffold geometry was chosen and the design files, which were previously created using SolidWorks software (Dassault Systèmes SolidWorks Corp., Waltham, Mass.), were obtained. The chosen scaffold geometry was a helical sleeve design, with 350 µm square pores and supports on the bottom. (See FIG. 15) 50 mL of resin was poured into the basement plate of the Perfactory™ 3 3D printer. The build file was sent from the computer to the printer using Perfactory™ Software Suite 2.6 (EnvisionTEC, Dearborn, Mich.). The Perfactory™ 3D printer was operated using a 75 mm focal length lens. This allowed for a native resolution of 42 µm in the XY-plane. The enhanced resolution module (ERM), which allows for a native resolution of 21 µm in the XY-plane, was not used for this study. The printing job completed in 4 hours and 11 minutes. Once the scaffolds were finished, the build plate containing the attached scaffolds was removed from the printer. The scaffolds were washed, first with 70% acetone, to remove any uncured resin from within the pores of the scaffolds. The scaffolds were then briefly rinsed with 70% EtOH followed by a rinse with dH$_2$O. Compressed air was used to gently dry the scaffolds. The scaffolds were then removed from the build plate using a razor blade (a plastic card or scraper may also be used). The scaffolds were placed onto microscope slides, standing upright, and put into the UV chamber for an additional 8 hours to complete further cross-linking.

Example 13

3D Photochemical Printing

To insure that resorbable poly(propylene fumarate) (PPF) that was synthesized with the ring opening method could be 3D printed, we tested material with a molecular mass of 1496 Da for 3D printing tests in an EnvisionTEC (Dearborn, Mich.) Perfactory P3 photocrosslinking-based device. Diethyl fumarate (DEF) (Sigma-Aldrich, St. Louis, Mo.) was added to the PPF in a 1:3 mass ratio in order to reduce the viscosity of the polymer. This mixture was then stirred and heated at 200° F. in a fume hood. A resin suitable for photocrosslinking was then created from the 1:3 DEF:PPF mixture by adding the photoinitiators Irgacure 819 and Irgacure 784 (BASF, Ludwigshafen, Germany) as well as oxybenzone (Sigma-Aldrich), and additional DEF to bring the final resin composition to 1:1 DEF:PPF, 3% Irgacure 819, 0.4% Irgacure 784, and 0.7% oxybenzone. DEF was used as the solvent, along with heat, to dissolve the photoinitiators and oxybenzone prior to their addition to the 3:1 PPF:DEF resin.

Figure 16A:
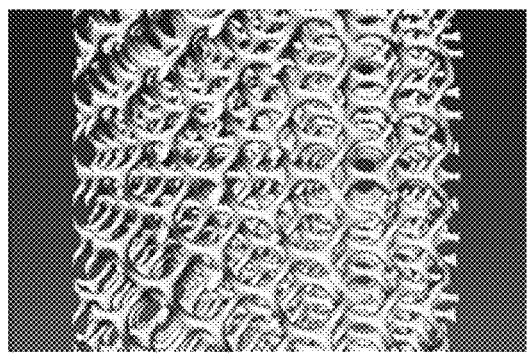
FIG. 16A-B are images showing a PPF scaffold created in SolidWorks™ CAD software using the Schoen Gyroid Triply Periodic Minimal Surface with 125 µm strut thickness, 600 µm pore diameter, and 93.5% porosity.
Figure 16B:
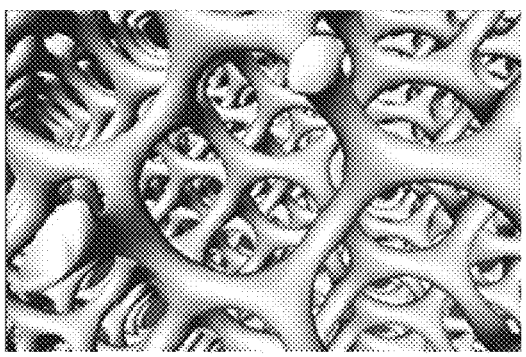
Figure 16C:
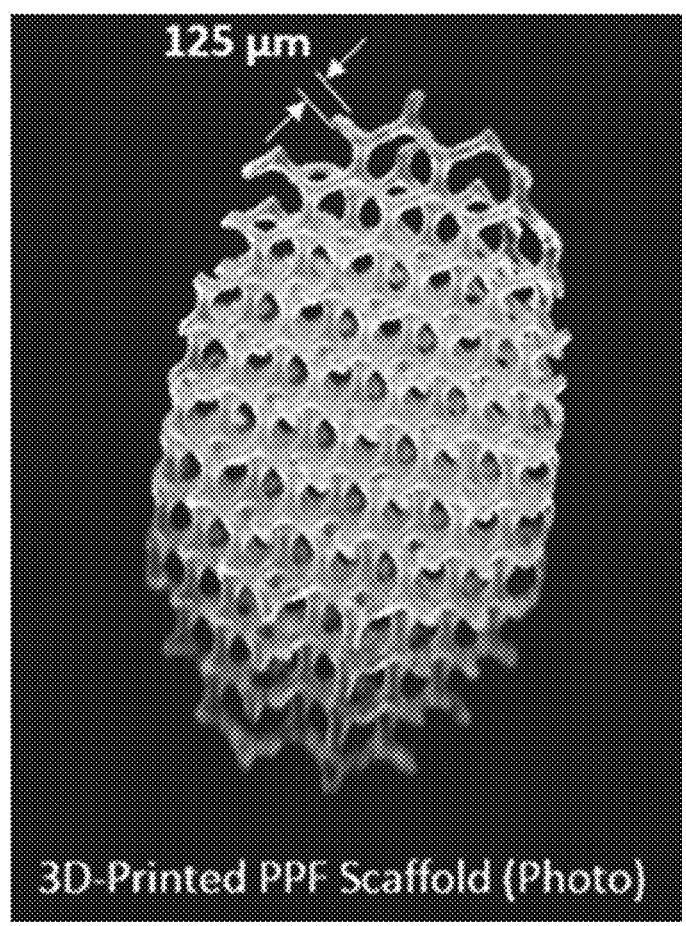
FIG. 16C is an image of a PPF scaffold created in SolidWorks™ computer assisted design software and 3D printed using a Perfactory™ P3 printer.

A porous, cylindrical scaffold CAD file using the Schoen Gyroid triply periodic minimal surface pore geometry with 125 µm strut thickness, pore diameter of 600 µm, and porosity of 93.5% was created in was created in SolidWorks (Dassault Systemes, Waltham, Mass.). The CAD file was 3D printed using the previously described PPF-containing resin using an EnvisionTEC (Dearborn, Mich.) Perfactory P3 3D printer (See FIG. 16A-C). No morphometric analysis of the scaffolds was done (those comparisons are currently underway), however the 3D printing accuracy was found on quick inspection with a caliper to be identical to scaffolds using PPF synthesized by the step growth method.

Example 14

Scaffold Imaging

The scaffolds were imaged using an Olympus Stereoscope (Center Valley, Pa.) to depict the scaffold features and individually cured layers in greater detail. (See FIG. 15)

Example 15

Thin Films of PPF

The resins of Example 3 above were heated to ensure homogeneity before it was used to create the thin films. To create the thin films, a transfer pipette was used to place 5-7 drops of the resin down the middle of a glass slide, in the longitudinal direction. A second glass slide was slowly placed on top of the first slide, ensuring that no air bubbles formed while the resin was spread evenly between the two slides. The slides were placed in a UV chamber (3D Systems, Rock Hill, S.C.) for 30 minutes. After this time, the slides were removed and a razor blade was used to peel the thin films of partially cross-linked PPF resin off of the slides. The films were cut into squares that measured 1 cm along each edge. The cut squares were sandwiched between two slides, to prevent curling, and put back into the UV chamber for 7.5 hours to complete further cross-linking.

Example 16

Washing/Sterilization

Before beginning the direct contact assay, the thin films were washed and sterilized. The washing protocol began with a 15 min wash in Dulbecco's phosphate buffered saline (DPBS) (Life Technologies, Carlsbad, Calif.) to remove surface debris introduced during production. This was followed by three separate washes in 70% acetone for durations of 30 minutes, 20 minutes, and 10 minutes. Between acetone washes, the films were soaked in DPBS to remove excess acetone from the films and to prevent them from drying out. The protocol is finished by completing two more washes in DPBS, 15 min each. This entire process was repeated, so that the thin films went through the washing protocol twice. After washing, the thin films were soaked in DPBS for 72 h in an incubator at 37° C., 5% $CO_2$.

Example 17

Cell Culture

Murine fibroblasts, L929 cell line (Sigma-Aldrich, St. Louis, Mo.), were used for in vitro cytotoxicity analysis in line with ISO Standard 10993-5, which outlines standards for direct contact assays. L929 cells were cultured with Minimum Essential Medium (MEM) (Sigma-Aldrich, St. Louis, Mo.) containing 10% horse serum (Sigma-Aldrich, St. Louis, Mo.) and 1% Penicillin-Streptomycin (Life Technologies, Carlsbad, Calif.), as outlined by the manufacturer. Cells were plated at 75,000 cells per well into a 24-well polystyrene cell culture plate (Corning Life Sciences, Corning, N.Y.). The cells were grown to ~80% confluency on the coverslips prior to beginning the direct contact assay. Coverslips were used so that they could be removed upon staining and mounted to a microscope slide for examination under a fluorescence microscope.

Example 18

Cytotoxicity Assay

A direct contact test was conducted in accordance with ISO Standard 10993-5 using the cell culture of Example 17, above. Cytotoxicity was assessed at 24, 48, and 72-h. To initiate the test, the media was aspirated from the wells containing cells. Then, a thin film of PPF was placed on top of the cell monolayers in each well. Around 150 µL of media was then added back into each well—enough to cover the well, but keep the thin film from floating above the cell monolayer. The cells and thin films were then incubated at 37° C. and 5% $CO_2$ for 24, 48, or 72 h. Afterwards, the cytotoxicity of the material was assessed through fluorescence microscopy and analyzed as described below. (See, Examples 19 and 20). The cells were incubated with live/dead solution which causes dead cells to appear red and live cells to appear green under fluorescence. Imaging was done and results were assessed qualitatively in the images where green=live cells and red=dead cells. From these assessments, it was determined that the PPF polymers tested were not toxic.

Example 19

Microscopy

The scaffolds were imaged using an Olympus Stereoscope (Center Valley, Pa.) to depict the scaffold features and individually cured layers in greater detail. (See FIG. 15). As set forth above, live/dead staining was performed to assess the cytotoxicity of the PPF. A solution containing 2 µM calcein AM and 4 µM ethidium homodimer-1 (EthD-1) was prepared in DPBS using a cytotoxicity kit (Life Technologies, Carlsbad, Calif.). Wells containing thin films as well as those serving as controls were incubated with 150 µL of live/dead solution at room temperature for 30 minutes in dark conditions. Cells that were cultured as mentioned previously and then incubated in 70% methanol for 30 minutes prior to incubation in live/dead solution were used as a positive, cytotoxic control. As a negative, noncytotoxic control, cells were cultured in normal conditions on polystyrene culture plates prior to live/dead staining and received no other treatment. After incubation with the live/dead solution, images were taken with an Olympus CKX41 fluorescence microscope outfitted with a 12.8 MP digital camera (Olympus, Center Valley, Pa.) as set forth in Example 20, below.

Example 20

Fluorescence Imaging

Live/dead staining was performed on the coverslips to assess the cytotoxicity of the PPF on the cells culture of Example 17. A solution containing 2 µM calcein AM and 4 µM ethidium homodimer-1 (EthD-1) was prepared in DPBS using a cytotoxicity kit (Life Technologies, Carlsbad, Calif.). The coverslips with attached cells were incubated with the live/dead solution at room temperature for 30 minutes in dark conditions. Cells that were incubated in 70% methanol for 30 min were used as a positive, cytotoxic control. As a negative, noncytotoxic control, cells were cultured in normal conditions on HDPE culture plates. After incubation with the live/dead solution, coverslips were removed from the well plate and mounted onto microscope slides for imaging. Images were taken with an inverted Diaphot-TMD microscope (Nikon, Chiyoda, Tokyo, Tokyo) outfitted with an epi-fluorescence kit (Nikon, Chiyoda, Tokyo, Tokyo) and a 5.0 MP CCD digital camera (Amscope, Irvine, Calif.). The results were assessed qualitatively from the images where the live cells fluoresce green and the dead cells fluoresce red. From these assessments, it was determined that the PPF polymers tested were not toxic.

Example 21

Degradation of 3D Printed Porous PPF Scaffolds

Figure 17A:
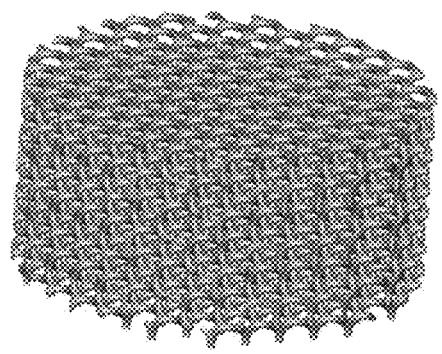
FIGS. 17A-C are computer assisted drafting (CAD) images showing a front perspective view (FIG. 17A), side view (FIG. 17B), and top view (FIG. 17C) of a 3D object made by a 3D printing process using a PPF polymer made according to the one or more embodiments of the present invention.
Figure 17B:
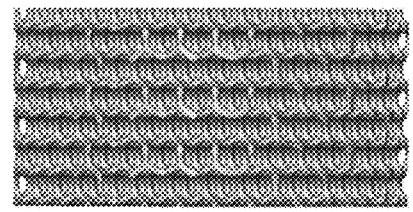
Figure 17C:
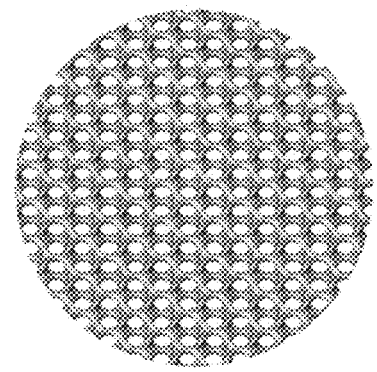
Figure 17D:
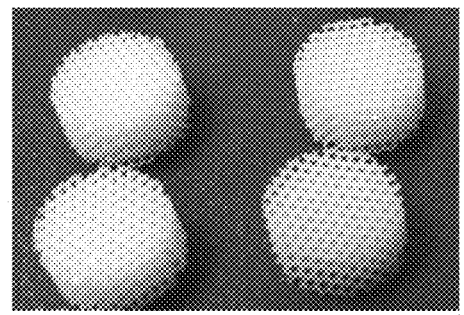
FIG. 17D is a photograph taken of a 3D object made by a 3D printing process using a PPF polymer made according to the one or more embodiments of the present invention.
Figure 17E:
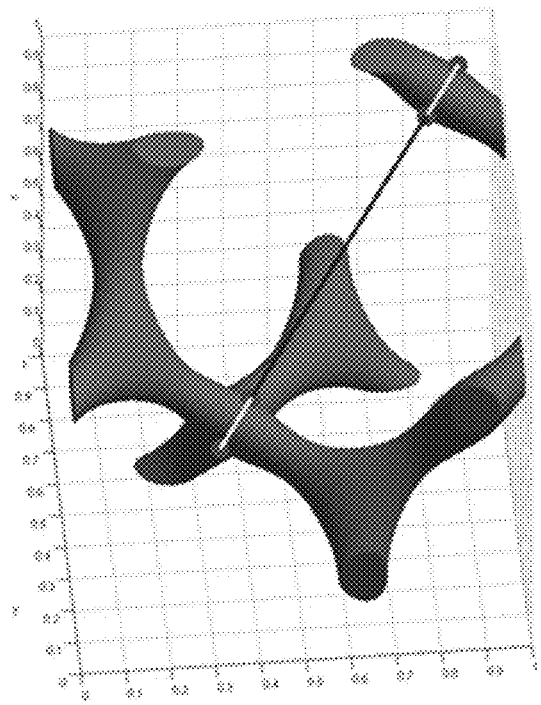
FIG. 17E is a schematic representation of the strut and pore structure of a 3D object made by a 3D printing process using a PPF polymer made according to the one or more embodiments of the present invention.
Figure 18:
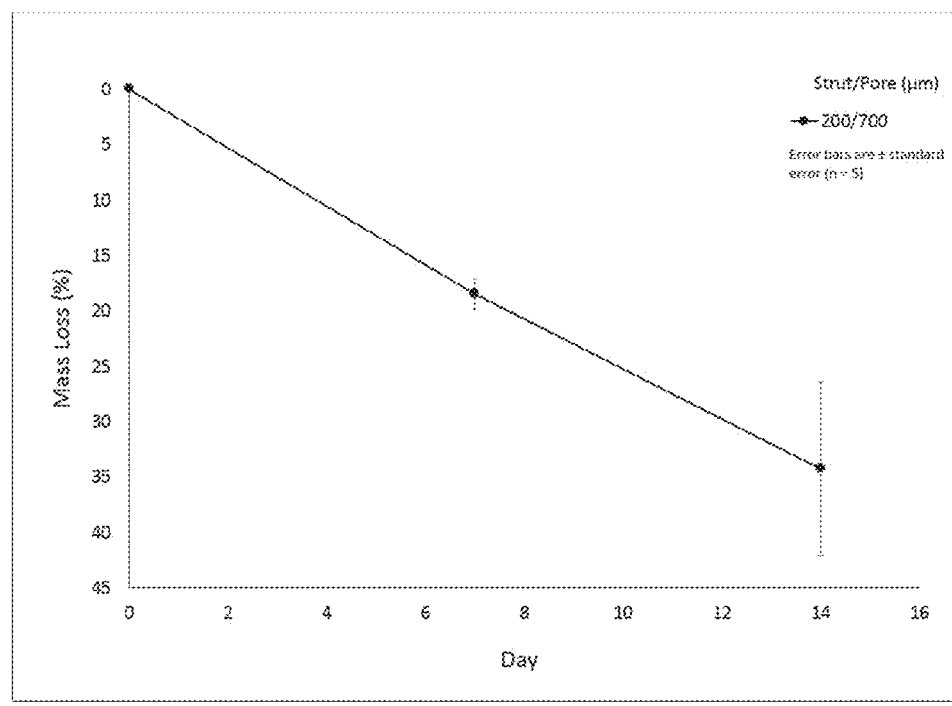
FIG. 18 is graph showing the results of a 14 day degradation experiment done on a 3D object made by a 3D printing process using a PPF polymer made according to the one or more embodiments of the present invention.
Figure 19:
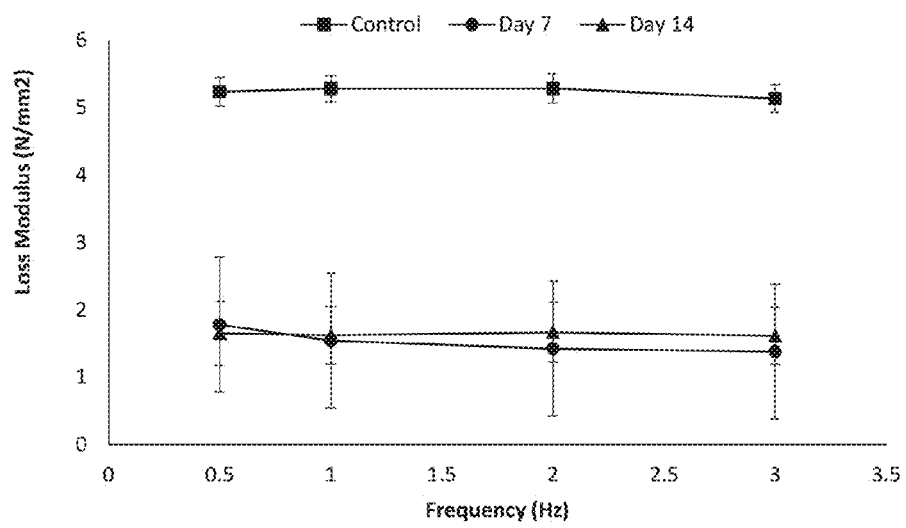
FIG. 19 is graph showing the results of dynamic mechanical testing done on a 3D object made by a 3D printing process using a PPF polymer made according to the one or more embodiments of the present invention showing the loss modulus as a function of the frequency.
Figure 20:
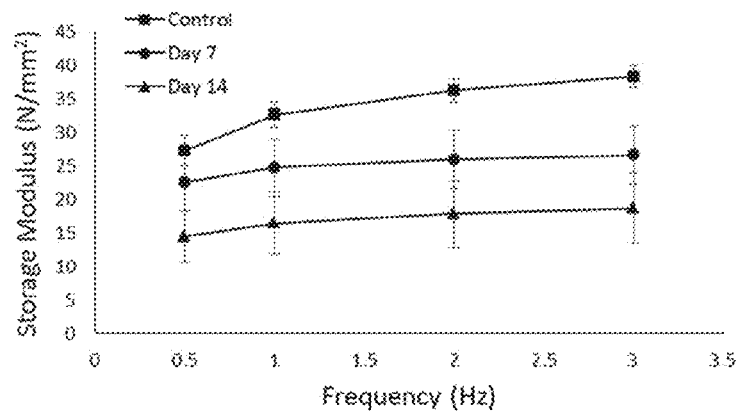
FIG. 20 is graph showing the results of dynamic mechanical testing done on a 3D object made by a 3D printing process using a PPF polymer made according to the one or more embodiments of the present invention showing the storage modulus as a function of the frequency.
Figure 21:
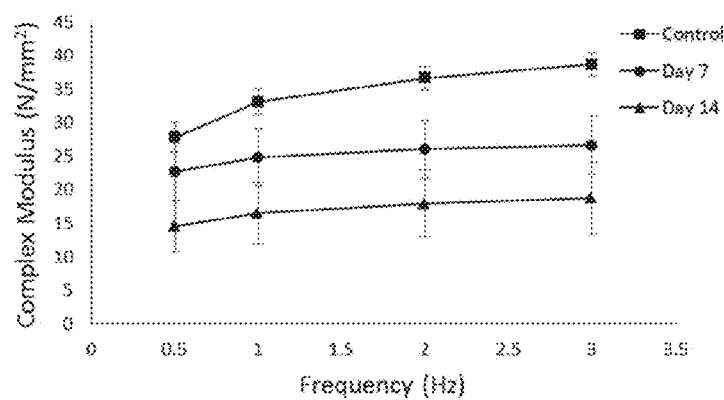
FIG. 21 is graph showing the results of dynamic mechanical testing done on a 3D object made by a 3D printing process using a PPF polymer made according to the one or more embodiments of the present invention showing the complex modulus as a function of the frequency.
Figure 22:
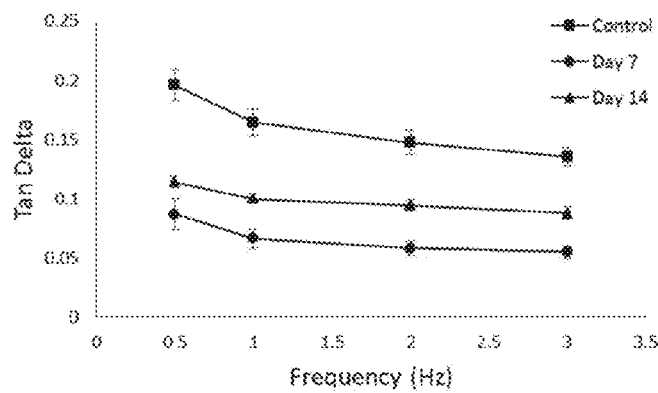
FIG. 22 is graph showing the results of dynamic mechanical testing done on a 3D object made by a 3D printing process using a PPF polymer made according to the one or more embodiments of the present invention showing Tan Δ as a function of the frequency.

Porous 3D scaffolds were printed using the procedure set forth in Example 12 above using a PPF polymer according to one embodiment of the present invention. The PPF Polymer had a number average molecular weight $M_n$ of 1260 Daltons and a $Đ_m$ of 1.5 and was synthesized as described in Examples 1-3 above. The resin used to produce the porous 3D scaffolds shown in FIGS. 17A-E was made using a solution having a 1:1 mass ratio of PPF polymer to DEF and contained 30.0 mg/g(DEF+PPF) of Irgacure-819 (BAPO) (BASF, Germany) as a photo-initiator, 4.0 mg/g (DEF+PPF) of I-784 (BASF, Germany) as a photo-initiator, and 7.0 mg/g(DEF+PPF) of 2-Hydroxy-4-methoxybenzophenone (also known as oxybenzone or HMB) (Sigma-Aldrich Co., St. Louis, Mo.) as a light absorbing dye. The 3D printed scaffolds were generally cylindrical with a Schoen gyroid porous architecture (See FIGS. 17A-D). They are 88.2% porous with a strut diameter of about 200 μm and a pore diameter of about 700 μm. See FIG. 17E. The 3D printed scaffolds had a height of about 5 mm and a diameter of about 10 mm and the shrinkage when cured was X-Y=17.16±0.26%; Z=13.96±0.32% (actual size after shrinkage: h=4.30±0.02; Ø=8.28±0.03). Five 3D printed scaffolds were weighed and then immersed for 7 days in a 0.1 M NaOH (13.0 pH) solution under static conditions at 37° C. (n=5) A second set of five 3D printed scaffolds (K-O) were weighed and then immersed for 14 days in a 0.1 M NaOH (13.0 pH) solution under static conditions at 37° C. The treated samples (A-E) and (K-O) were weighed and the degradation rate determined and plotted on FIG. 18. Five other undegraded samples ($C_1$-$C_5$) were used as a control.

Example 22

Dynamic Mechanical Analysis

Samples $C_1$-$C_5$ (control: undegraded), A-E (treated), and (K-O) (described in Example 21 above) were dried and their dynamic mechanical characteristics (loss modulus, storage modulus, Tan Δ) analyzed using a BOSE ElectroForce 3230 machine equipped with a 450 N load cell. The results are reported in FIGS. 19-22.

Example 23

Compression to Failure

Figure 23:
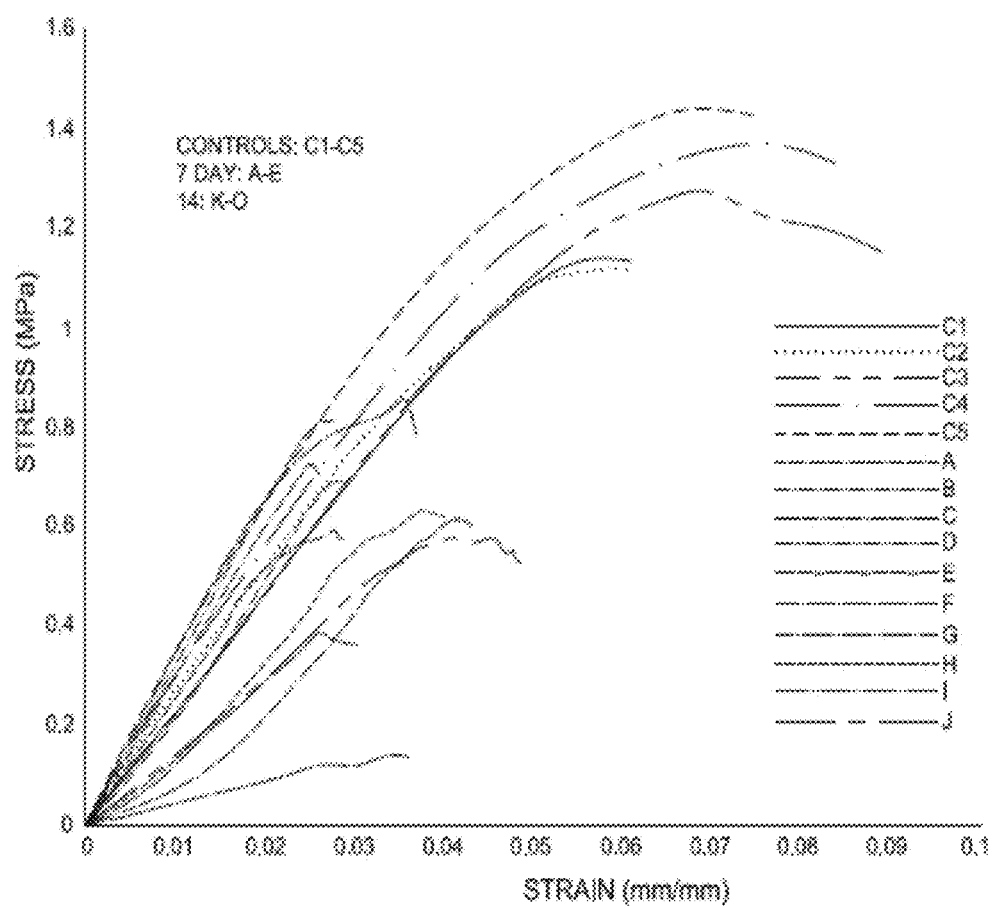
FIG. 23 is graph showing the results of compression to failure testing done on a 3D object made by a 3D printing process using a PPF polymer made according to the one or more embodiments of the present invention showing the stress as a function of strain for undegraded samples (C1-C5), samples degraded for 7 days (A-E), and samples degraded for 14 days (K-O).
Figure 24:
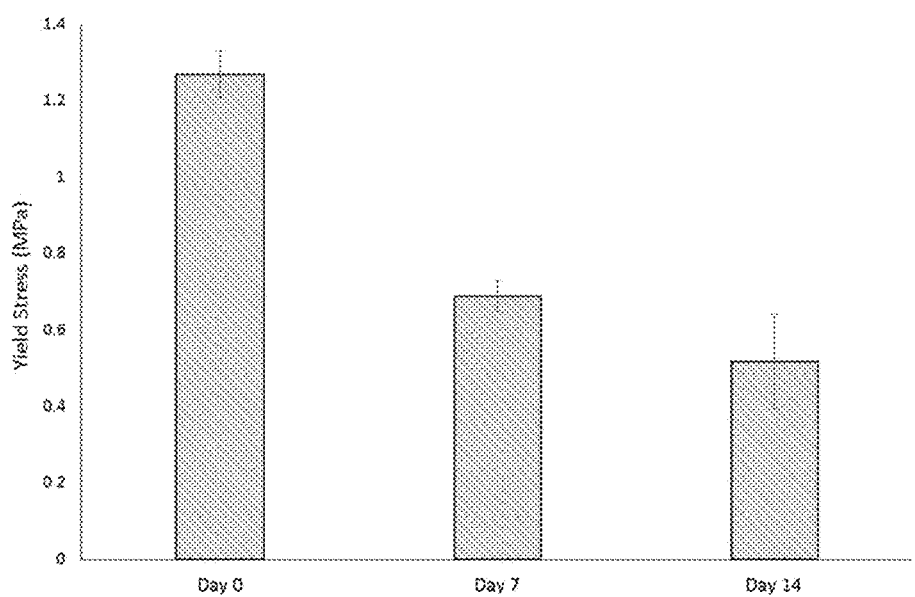
FIG. 24 is bar graph showing the results of compression to failure testing done on a 3D object made by a 3D printing process using a PPF polymer made according to the one or more embodiments of the present invention showing the Yield Stress for undegraded samples, samples degraded for 7 days, and samples degraded for 14 days.

Samples $C_1$-$C_5$ (control: undegraded) and A-E (treated) (described in Example 21 above) were then compressed to failure using the same BOSE ElectroForce 3230 machine and 450 N load cell at a strain rate of 1.0%/sec and their stress and strain characteristics analyzed. The Average Young's Modulus was estimated to be 26 MPa. The yield stress ($\sigma_y$) for the control samples ($C_1$-$C_5$) was 1.27±0.06 MPa. For the 7-day treated samples (A-E) $\sigma_y$ was 0.69±0.04 Mpa and for the 14-day treated samples (K-O), $\sigma_y$ was 0.51±0.12. The results are shown in FIGS. 23 and 24.

In light of the foregoing, it should be appreciated that the present invention significantly advances the art by providing a PPF polymer (and related method of making a PPF polymer) that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method for making a poly(propylene fumarate) polymer that: has a number average molecular weight (Mn) of from about 450 Daltons to about 3400 Daltons; has a molecular mass distribution (Ð m) of from 1.0 to 2.0; and contains less than 1% w/w of poly(maleic anhydride-co-propylene oxide) polymer chains, and is used in compositions for 3D printing, said method comprising reacting maleic anhydride and propylene oxide by a ring opening polymerization reaction in the presence of a magnesium initiator to form a poly(maleic anhydride-co-propylene oxide) polymer and then isomerizing said poly(maleic anhydride-co-propylene oxide) polymer to produce a poly(propylene fumarate) polymer.

2. The .method. for making a poly(propylene fumarate) polymer of claim 1 further comprising:
   A) dissolving the maleic anhydride and the propylene oxide in a solvent under an inert atmosphere;
   B) adding a magnesium initiator to the solution of step A;
   C) heating the mixture of step B to a temperature of from about 60° C. to about 120° C. for a period of from about 0.5 hours to about 100 hours to produce a poly(maleic anhydride-co-propylene oxide) polymer;
   D) collecting and purifying the poly(maleic anhydride-co-propylene oxide) polymer;
   E) dissolving the poly(maleic ride-co-propylene oxide) in a solvent and adding a catalyst;
   F) heating the mixture of step E to a temperature of from about 5° C. to about 80° C. for a period of from about 5 hours to about 100 hours to produce a polypropylene fumarate) polymer.

3. The method of claim 2 wherein the solvent of step A is selected from the group consisting of toluene, tetrahydrofuran (THF), dioxane, and combinations thereof.

4. The method of claim 2 wherein he magnesium initiator of step B is magnesium ethoxide (Mg(OEt)$_2$).

5. The method of claim 2 wherein the molar ratio of either the maleic anhydride or the propylene oxide of step A to the initiator of step B is from about 3:1 to about 400:1.

6. The method of claim 2, wherein Step D further comprise:
   1) cooling the mixture of step C under an inert atmosphere;
   2) evaporating the volatile compounds from the mixture of step (1);
   3) adding chloroform or dichloromethane to the mixture of step (2);

4) washing the solution of step (3) with an aqueous solution, thereby forming an organic layer and an aqueous layer;
5) collecting the organic layer of step (4) and adding it into a non-polar organic solvent to cause the poly (maleic anhydride-co-propylene oxide) polymer to precipitate;
6) collecting the poly(maleic anhydride-co-propylene oxide) polymer;
7) dissolving the poly(maleic anhydride-co-propylene oxide) polymer in a solvent and concentrating the solution by evaporation; and
8) drying the concentrated solution of step (7) under a vacuum, to produce a purified poly(maleic anhydride-co-propylene oxide) polymer.

7. The method of claim 6 wherein the step of evaporating the volatile compounds from the mixture of step (1)(step (2) by is performed by distillation or reduced pressure.

8. The method of claim 2 wherein the solvent of step E is selected from the group consisting of chloroform, tetrahydrofuran (THF), dioxane, and combinations thereof.

9. The method of claim 2 wherein the catalyst of step E is diethylamine.

10. The method of claim 2 further comprising collecting and purifying the poly(propylene fumarate) polymer.

11. The method of claim 10 comprising:
a) concentrating the mixture of Step F by evaporation;
b) washing the mixture of step (a) with a buffered aqueous solution to remove the catalyst, thereby forming an forming an organic layer and an aqueous layer;
c) collecting the organic layer;
d) concentrating the organic layer by evaporation;
e) adding an inorganic drying agent, acidic proton or molecular sieve to remove remaining water;
f) filtering the mixture of step (e) to remove the inorganic drying agent, acidic proton or molecular sieve;
g) adding the mixture of step (f) into non-polar organic solvent to cause the poly(propylene fumarate) polymer to precipitate;
h) collecting the poly(propylene fumarate) polymer of step (g);
i) and drying the poly(propylene fumarate) polymer of step (f) under a vacuum, to produce a purified poly (propylene fumarate) polymer.

12. The method of claim 10 wherein the mixture of step (a) is concentrated by rotary evaporation or reduced pressure.

13. The method of claim 10 wherein the buffered aqueous solution of step (b) comprises a phosphate buffered saline solution.

14. The method of claim 10 wherein the organic layer of step (d) is concentrated by distillation, rotary evaporation or reduced pressure.

15. The method of claim 10 wherein sodium sulfate is added to the mixture of step (d) to remove remaining water.

16. The method of claim 10 wherein non-polar organic solvent of step (g) comprises hexane.

* * * * *

UNITED STATES PATENT AND TRADEMARK OFFICE
CERTIFICATE OF CORRECTION

| | |
|---|---|
| PATENT NO. | : 10,465,044 B2 |
| APPLICATION NO. | : 15/527484 |
| DATED | : November 5, 2019 |
| INVENTOR(S) | : Matthew Becker, Howard Dean and Yuanyuan Luo |

Page 1 of 1

It is certified that error appears in the above-identified patent and that said Letters Patent is hereby corrected as shown below:

Column 1, Line 22 add Government Support Clause:
--This invention was made with government support under grant numbers DE013740 and AR061460 awarded by the National Institutes of Health. The government has certain rights in the invention.--

Signed and Sealed this
Sixth Day of October, 2020

Andrei Iancu
*Director of the United States Patent and Trademark Office*